United States Patent [19]
Wos et al.

[11] Patent Number: 6,107,338
[45] Date of Patent: *Aug. 22, 2000

[54] AROMATIC $C_{16}$-$C_{20}$-SUBSTITUTED TETRAHYDRO PROSTAGLANDINS USEFUL AS FP AGONISTS

[75] Inventors: John August Wos, Cincinnati; Mitchell Anthony deLong, West Chester; Jack S. Amburgey, Jr., Loveland, all of Ohio; Haiyan George Dai, Drexel Hill, Pa.; Cynthia Jean Miley; Biswanath De, both of Cincinnati, Ohio

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 09/148,374

[22] Filed: Sep. 4, 1998

Related U.S. Application Data

[60] Provisional application No. 60/058,246, Sep. 9, 1997.

[51] Int. Cl.[7] ................. C07C 405/00; A61K 31/5575
[52] U.S. Cl. ............... 514/530; 514/570; 514/438; 549/79; 560/60; 562/470; 562/621
[58] Field of Search ................. 560/121, 118, 560/60; 562/470, 621; 549/79; 514/530, 570, 438

[56] References Cited

U.S. PATENT DOCUMENTS 4,011,262   3/1977   Hess .......................... 560/118

FOREIGN PATENT DOCUMENTS

| | | |
|---|---|---|
| 0 857 718 A1 | 6/1997 | European Pat. Off. . |
| 002460990 | 7/1976 | Germany . |
| 1 456 838 | 11/1972 | United Kingdom . |
| 1 542 569 | 8/1976 | United Kingdom . |
| WO 92/02495 | 2/1992 | WIPO . |
| WO 95/18102 | 7/1995 | WIPO . |
| WO 97/23225 | 7/1997 | WIPO . |
| WO 97/31895 | 9/1997 | WIPO . |
| WO 98/12175 | 3/1998 | WIPO . |
| WO 98/20880 | 5/1998 | WIPO . |
| WO 98/20881 | 5/1998 | WIPO . |
| WO 98/21180 | 5/1998 | WIPO . |
| WO 98/50024 | 11/1998 | WIPO . |

OTHER PUBLICATIONS

Lijebris, C., Selen, G., Resul, B., Stjernschantz, J., and Hacksell, U., "Dervatives of 17–Phenyl–18, 19,20–trinor-prostaglandin $F_{2\alpha}$ Isopropyl Ester: Potential Antiglaucoma Agents", *Journal of Medicinal Chemistry*, vol. 38, No. 2, (1995).

Bundy, G. L., and Lincoln, F. H., "Synthesis of 17–Phenyl–18, 19, 20–Trinoprostaglandins I. The $PG_1$ Series", *Prostaglandins*, vol. 9, No. 1, (Jan. 1975).

*Primary Examiner*—Robert Gerstl
*Attorney, Agent, or Firm*—James C. Kellerman; Carl J. Roof

[57] ABSTRACT

The invention provides novel PGF analogs. In particular, the present invention relates to compounds having a structure according to the following formula:

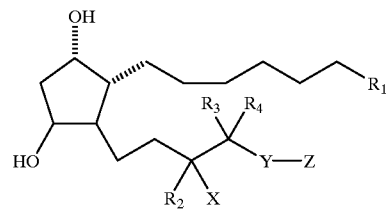

wherein $R_1$, $R_2$, $R_3$, $R_4$, X, Y, and Z are defined below.

This invention also includes optical isomers, diastereomers and enantiomers of the formula above, and pharmaceutically-acceptable salts, biohydrolyzable amides, esters, and imides thereof.

The compounds of the present invention are useful for the treatment of a variety of diseases and conditions, such as bone disorders and glaucoma. Accordingly, the invention further provides pharmaceutical compositions comprising these compounds. The invention still further provides methods of treatment for bone disorders and glaucoma using theses compounds or the compositions containing them.

26 Claims, No Drawings

AROMATIC $C_{16}$-$C_{20}$-SUBSTITUTED TETRAHYDRO PROSTAGLANDINS USEFUL AS FP AGONISTS

CROSS REFERENCE

This application claims priority under Title 35, United States Code 119(e) from Provisional Application Ser. No. 60/058,246, filed Sep. 9, 1997.

TECHNICAL FIELD

The subject invention relates to certain novel analogs of the naturally occurring prostaglandins. Specifically, the subject invention relates to novel Prostaglandin F analogs. The subject invention further relates to methods of using said novel Prostaglandin F analogs. Preferred uses include methods of treating bone disorders and glaucoma.

BACKGROUND OF THE INVENTION

Naturally occurring prostaglandins (PGA, PGB, PGE, PGF, and PGI) are C-20 unsaturated fatty acids. $PGF_{2\alpha}$, the naturally occurring Prostaglandin F in humans, is characterized by hydroxyl groups at the $C_9$ and $C_{11}$ positions on the alicyclic ring, a cis-double bond between $C_5$ and $C_6$, and a trans-double bond between $C_{13}$ and $C_{14}$. Thus $PGF_{2\alpha}$ has the following formula:

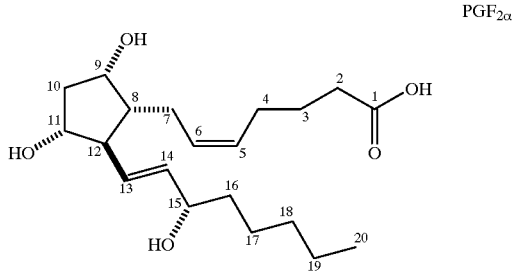

$PGF_{2\alpha}$

Analogs of naturally occurring Prostaglandin F have been disclosed in the art. For example, see U.S. Pat. No. 4,024,179 issued to Bindra and Johnson on May 17, 1977; German Patent No. DT-002,460,990 issued to Beck, Lerch, Seeger, and Teufel published on Jul. 1, 1976; U.S. Pat. No. 4,128,720 issued to Hayashi, Kori, and Miyake on Dec. 5, 1978; U.S. Pat. No. 4,011,262 issued to Hess, Johnson, Bindra, and Schaaf on Mar. 8, 1977; U.S. Pat. No. 3,776,938 issued to Bergstrom and Sjovall on Dec. 4, 1973; P. W. Collins and S. W. Djuric, "Synthesis of Therapeutically Useful Prostaglandin and Prostacyclin Analogs", Chem. Rev. Vol. 93 (1993), pp. 1533–1564; G. L. Bundy and F. H. Lincoln, "Synthesis of 17-Phenyl-18,19,20-Trinorprostaglandins: I. The $PG_1$ Series", Prostaglandins, Vol. 9 No. 1 (1975), pp. 1–4; W. Bartman, G. Beck, U. Lerch, H. Teufel, and B. Scholkens, "Luteolytic Prostaglandins: Synthesis and Biological Activity", Prostaglandins, Vol. 17 No. 2 (1979), pp. 301–311; C. Iiljebris, G. Selen, B. Resul, J. Sternschantz, and U. Hacksell, "Derivatives of 17- Phenyl-18,19,20-trinorprostaglandin $F_2\alpha$ Isopropyl Ester: Potential Antiglaucoma Agents", Journal of Medicinal Chemistry, Vol. 38 No. 2 (1995), pp. 289–304.

Naturally occurring prostaglandins are known to possess a wide range of pharmacological properties. For example, prostaglandins have been shown to: relax smooth muscle, which results in vasodilatation and bronchodilatation, to inhibit gastric acid secretion, to inhibit platelet aggregation, to reduce intraocular pressure, and to induce labor. Although naturally occurring prostaglandins are characterized by their activity against a particular prostaglandin receptor, they generally are not specific for any one prostaglandin receptor. Therefore, naturally-occurring prostaglandins are known to cause side effects such as inflammation, as well as surface irritation when administered systemically. It is generally believed that the rapid metabolism of the naturally occurring prostaglandins following their release in the body limits some of the effects of the prostaglandin to a local area. This effectively prevents the prostaglandin from stimulating prostaglandin receptors throughout the body and causing the effects seen with the systemic administration of naturally occurring prostaglandins.

Prostaglandins, especially prostaglandins of the E series (PGE), are known to be potent stimulators of bone resorption. $PGF_{2\alpha}$ has also been shown to be a stimulator of bone resorption but not as potent as $PGE_2$. Also, it has been demonstrated the $PGF_{2\alpha}$ has little effect on bone formation. It has been suggested that some of the effects of $PGF_{2\alpha}$ on bone resorption, formation and cell replication may be mediated by an increase in endogenous $PGE_2$ production.

In view of both the wide range of pharmacological properties of naturally occurring prostaglandins and of the side effects seen with the systemic administration of these naturally occurring prostaglandins, attempts have been made to prepare analogs to the naturally occurring prostaglandins that are selective for a specific receptor or receptors. A number of such analogs have been disclosed in the art. Though a variety of prostaglandin analogs have been disclosed, there is a continuing need for potent, selective prostaglandin analogs for the treatment of a variety diseases and conditions.

SUMMARY OF THE INVENTION

The invention provides novel PGF analogs. In particular, the present invention relates to compounds having a structure according to the following formula:

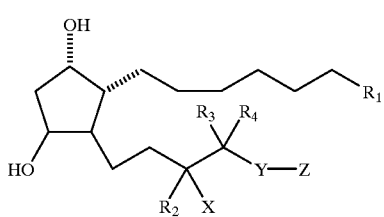

wherein $R_1$, $R_2$, $R_3$, $R_4$, X, Y, and Z are defined below.

This invention also includes optical isomers, diastereomers and enantiomers of the formula above, and pharmaceutically-acceptable salts, biohydrolyzable amides, esters, and imides thereof.

The compounds of the present invention are useful for the treatment of a variety of diseases and conditions, such as bone disorders and glaucoma. Accordingly, the invention further provides pharmaceutical compositions comprising these compounds. The invention still further provides methods of treatment for bone disorders and glaucoma using theses compounds or the compositions containing them.

DETAILED DESCRIPTION OF THE INVENTION

Terms and Definitions

"Acyl' is a group suitable for acylating a nitrogen atom to form an amide or carbamate or an oxygen atom to form an ester group. Preferred acyl groups include benzoyl, acetyl, tert-butyl acetyl, para-phenyl benzoyl, and trifluoroacetyl. More preferred acyl groups include acetyl and benzoyl. The most preferred acyl group is acetyl.

"Alkyl" is a saturated or unsaturated hydrocarbon chain having 1 to 18 carbon atoms, preferably 1 to 12, more preferably 1 to 6, more preferably still 1 to 4 carbon atoms. Alkyl chains may be straight or branched. Preferred branched alkyl have one or two branches, preferably one branch. Preferred alkyl are saturated. Unsaturated alkyl have one or more double bonds and/or one or more triple bonds. Preferred unsaturated alkyl have one or two double bonds or one triple bond, more preferably one double bond. Alkyl chains may be unsubstituted or substituted with from 1 to about 4 substituents. Preferred alkyl are unsubstituted. Preferred substituted alkyl are mono-, di-, or trisubstituted. Preferred alkyl substituents include methyl, ethyl, propyl and butyl, halo, hydroxy, alkoxy (e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), aryl (e.g., phenyl, tolyl, alkyloxphenyl, alkyloxycarbonylphenyl, halophenyl), heterocyclyl, heteroaryl, amino (e.g., amino, mono- and di- $C_1$–$C_3$ alkanylamino, methylphenylamino, :methylbenzylamino, $C_1$–$C_3$ alkanylamido, carbamamido, ureido, guanidino).

"Aromatic ring" is an aromatic hydrocarbon ring system. Aromatic rings are monocyclic or fused bicyclic ring systems. Monocyclic aromatic rings contain from about 5 to about 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring. Aromatic rings may be unsubstituted or substituted with from 1 to about 4 substituents on the ring. Preferred aromatic ring substituents include: halo, cyano, alkyl, heteroalkyl, haloalkyl, phenyl, phenoxy or any combination thereof. More preferred substituents include halo and haloalkyl. Preferred aromatic rings include naphthyl and phenyl. The most preferred aromatic ring is phenyl.

"Bone disorder" means the need for bone repair or replacement. Conditions in which the need for bone repair or replacement may arise include: osteoporosis (including post menopausal osteoporosis, male and female senile osteoporosis and corticosteroid induced osteoporosis), osteoarthritis, Paget's disease, osteomalacia, multiple myeloma and other forms of cancer, prolonged bed rest, chronic disuse of a limb, anorexia, microgravity, exogenous and endogenous gonadal insufficiency, bone fracture, non-union, defect, prosthesis implantation and the like.

"Carbocyclic aliphatic ring" is a saturated or unsaturated hydrocarbon ring. Carbocyclic aliphatic rings are not aromatic. Carbocyclic aliphatic rings are monocyclic, or are fused, spiro, or bridged bicyclic ring systems. Monocyclic carbocyclic aliphatic rings contain from about 4 to about 10 carbon atoms, preferably from 4 to 7 carbon atoms, and most preferably from 5 to 6 carbon atoms in the ring. Bicyclic carbocyclic aliphatic rings contain from 8 to 12 carbon atoms, preferably from 9 to 10 carbon atoms in the ring. Carbocyclic aliphatic rings may be unsubstituted or substituted with from 1 to about 4 substituents on the ring. Preferred carbocyclic aliphatic ring substituents include: halo, cyano, alkyl, heteroalkyl, haloalkyl, phenyl, phenoxy or any combination thereof. More preferred substituents include halo and haloalkyl. Preferred carbocyclic aliphatic rings include cyclopentyl, cyclohexyl, cyclohexenyl, cycloheptyl, and cyclooctyl. More preferred carbocyclic aliphatic rings include cyclohexyl, cycloheptyl, and cyclooctyl. The most preferred carbocyclic aliphatic ring is cycloheptyl.

"Halo" is fluoro, chloro, bromo or iodo. Preferred halo are fluoro, chloro and bromo; more preferred are chloro and fluoro, especially fluoro.

"Haloalkyl" is a straight, branched, or cyclic hydrocarbon substituted with one or more halo substituents. Preferred haloalkyl are $C_1$–$C_{12}$; more preferred are $C_1$–$C_6$; more preferred still are $C_1$–$C_3$. Preferred halo substituents are fluoro and chloro. The most preferred haloalkyl is trifluoromethyl.

"Heteroalkyl" is a saturated or unsaturated chain containing carbon and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to about 4 substituents. Preferred heteroalkyl are unsubstituted. Preferred heteroalkyl substituents include methyl, ethyl, propyl and butyl, halo, hydroxy, alkoxy (e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), aryl (e.g., phenyl, tolyl, alkyloxphenyl, alkyloxycarbonylphenyl, halophenyl), heterocyclyl, heteroaryl, amino (e.g., amino, mono- and di- $C_1$–$C_3$ alkanylamino, methylphenylamino, methylbenzylamino, $C_1$–$C_3$ alkanylamido, carbamamido, ureido, guanidino).

"Heteroatom" is a nitrogen, sulfur, or oxygen atom. Groups containing more than one heteroatom may contain different heteroatoms.

"Heterocyclic aliphatic ring" is a saturated or unsaturated ring containing carbon and from 1 to about 4 heteroatoms in the ring, wherein no two heteroatoms are adjacent in the ring and no carbon in the ring that has a heteroatom attached to it also has a hydroxyl, amino, or thiol group attached to it. Heterocyclic aliphatic rings are not aromatic. Heterocyclic aliphatic rings are monocyclic, or are fused or bridged bicyclic ring systems. Monocyclic heterocyclic aliphatic rings contain from about 4 to about 10 member atoms (carbon and heteroatoms), preferably from 4 to 7, and most preferably from 5 to 6 member atoms in the ring. Bicyclic heterocyclic aliphatic rings contain from 8 to 12 member atoms, preferably 9 or 10 member atoms in the ring. Heterocyclic aliphatic rings may be unsubstituted or substituted with from 1 to about 4 substituents on the ring. Preferred heterocyclic aliphatic ring substituents include: halo, cyano, alkyl, heteroalkyl, haloalkyl, phenyl, phenoxy or any combination thereof. More preferred substituents include halo and haloalkyl. Preferred heterocyclic aliphatic rings include piperzyl, morpholinyl, tetrahydrofuranyl, tetrahydropyranyl and piperdyl.

"Heteroaromatic ring" is an aromatic ring system containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 member atoms in the ring. Bicyclic heteroaromatic rings contain from 8 to 12 member atoms, preferably 9 or 10 member atoms in the ring. Heteroaromatic rings may be unsubstituted or substituted with from 1 to about 4 substituents on the ring. Preferred heteroaromatic ring substituents include: halo, cyano, alkyl, heteroalkyl, haloalkyl, phenyl, phenoxy or any combination thereof. More preferred substituents include halo, haloalkyl, and phenyl. Preferred heteroaromatic rings include thienyl, thiazolo, purinyl, pyrimidyl, pyridyl, and furanyl. More preferred heteroaromatic rings include thienyl, furanyl, and pyridyl. The most preferred heteroaromatic ring is thienyl.

"Lower alkyl" is an alkyl chain radical comprised of 1 to 6, preferably 1 to 4 carbon atoms.

"Phenyl" is a six-membered monocyclic aromatic ring which may or may not be substituted with from about 1 to about 4 substituents. The substituents may be substituted at the ortho, meta or para position on the phenyl ring, or any combination thereof. Preferred phenyl substituents include: halo, cyano, alkyl, heteroalkyl, haloalkyl, phenyl, phenoxy or any combination thereof. More preferred substituents on the phenyl ring include halo and haloalkyl. The most preferred substituent is halo. The preferred substitution pattern on the phenyl ring is ortho or meta. The most preferred substitution pattern on the phenyl ring is ortho.

Compounds

The subject invention involves compounds having the following structure:

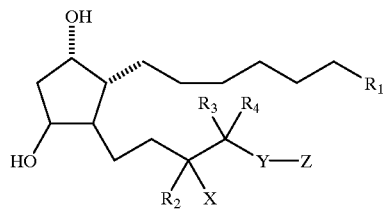

In the above structure, $R_1$ is $CO_2H$, $C(O)NHOH$, $CO_2R_5$, $CH_2OH$, $S(O)_2R_5$, $C(O)NHR_5$, $C(O)NHS(O)_2R_5$, or tetrazole; wherein $R_5$ is alkyl, heteroalkyl, carbocyclic aliphatic ring, heterocyclic aliphatic ring, aromatic ring, or heteroaromatic ring. Preferred $R_5$ is $CH_3$, $C_2H_5$, $C_3H_7$. Preferred $R_1$ is $CO_2H$, $C(O)NHOH$, $CO_2CH_3$, $CO_2C_2H_5$, $CO_2C_3H_7$, $CO_2C_4H_9$, $CO_2C_3H_7O_2$, and $C(O)NHS(O)_2R_5$. More preferred $R_1$ is $CO_2H$, $C(O)NHOH$, $CO_2CH_3$, and $CO_2C_3H_5$. Most preferred $R_1$ is $CO_2H$ and $CO_2CH_3$.

In the above structure, $R_2$ is H or lower alkyl. Preferred $R_2$ is H and $CH_3$. Most preferred $R_2$ is H.

In the above structure, X is $NR_6R_7$, $OR_8$, $SR_9$, $S(O)R_9$, $S(O)_2R_9$, or F; wherein $R_6$, $R_7$, and $R_8$ are independently selected from the group consisting of H, acyl, alkyl, heteroalkyl, carbocyclic aliphatic ring, heterocyclic aliphatic ring, aromatic ring, and heteroaromatic ring; and wherein $R_9$ is alkyl, heteroalkyl, carbocyclic aliphatic ring, heterocyclic aliphatic ring, aromatic ring, or heteroaromatic ring. Preferred $R_6$ and $R_7$ are H, $CH_3$ and $C_2H_5$. Preferred $R_8$ is H, $CH_3$, $C_2H_5$, and $C_3H_7$. Preferred $R_9$ is $CH_3$ and $C_2H_5$. Preferred X is $NR_6R_7$ and $OR_8$. Most preferred X is OH.

In the above structure, $R_3$ and $R_4$ are independently H, $CH_3$, $C_2H_5$, $OR_{10}$, $SR_{10}$, or OH, except that both $R_3$ and $R_4$ are not OH; wherein $R_{10}$ is alkyl, heteroalkyl, carbocyclic aliphatic ring, heterocyclic aliphatic ring, aromatic ring, or heteroaromatic ring, $R_{10}$ having from 1 to about 8 member atoms. Preferred $R_3$ and $R_4$ are H.

In the above structure, Y is $(CH_2)_n$; n being an integer from 0 to about 3. Preferred n is 0,1, and 2. Most preferred n is 1.

In the above structure, Z is carbocyclic aliphatic ring, heterocyclic aliphatic ring, monocyclic heteroaromatic ring, or substituted phenyl when n is 0, 2, or 3; and Z is carbocyclic aliphatic ring, heterocyclic aliphatic ring, or substituted phenyl when n is 1. Preferred Z is monocyclic. More preferred Z is substituted phenyl and monocyclic heteroaromatic ring. The most preferred Z is substituted phenyl and substituted or unsubstituted thienyl.

The invention also includes optical isomers, diastereomers and enantiomers of the above structure. Thus, at all stereocenters where stereochemistry is not defined ($C_{11}$, $C_{12}$, $C_{15}$, and $C_{16}$), both epimers are envisioned. Preferred stereochemistry at all such stereocenters of the compounds of the invention mimic that of naturally occurring $PGF_{22}$.

It has been discovered that the novel PGF analogs of the subject invention are useful for treating bone disorders, especially those that require a significant increase in bone mass, bone volume, or bone strength. Surprisingly, the compounds of the subject invention have been found to provide the following advantages over known bone disorder therapies: (1) An increase trabecular number through formation of new trabeculae; (2) An increase in bone mass and bone volume while maintaining a more normal bone turnover rate; and (3) An increase in bone formation at the endosteal surface without increasing cortical porosity.

In order to determine and assess pharmacological activity, testing of the subject compounds in animals is carried out using various assays known to those skilled in the art. For example, the bone activity of the subject compounds can be conveniently demonstrated using an assay designed to test the ability of the subject compounds to increase bone volume, mass, or density. An example of such assays is the ovariectomized rat assay.

In the ovariectomized rat assay, six-month old rats are ovariectomized, aged 2 months, and then dosed once a day subcutaneously with a test compound. Upon completion of the study, bone mass and/or density can be measured by dual energy x-ray absorptometry (DXA) or peripheral quantitative computed tomography (pQCT), or micro computed tomography (mCT). Alternatively, static and dynamic histomorphometry can be used to measure the increase in bone volume or formation.

Pharmacological activity for glaucoma can be demonstrated using assays designed to test the ability of the subject compounds to decrease intraocular pressure. Examples of such assays are described in the following reference, incorporated herein: C. Iiljebris, G. Selen, B. Resul, J. Sternschantz, and U. Hacksell, "Derivatives of 17- Phenyl-18,19,20-trinorprostaglandin $F_{2\alpha}$ Isopropyl Ester: Potential Antiglaucoma Agents", *Journal of Medicinal Chemistry*, Vol. 38 No. 2 (1995), pp. 289–304.

Compounds useful in the subject invention can be made using conventional organic syntheses. A particularly preferred synthesis is the following general reaction scheme:

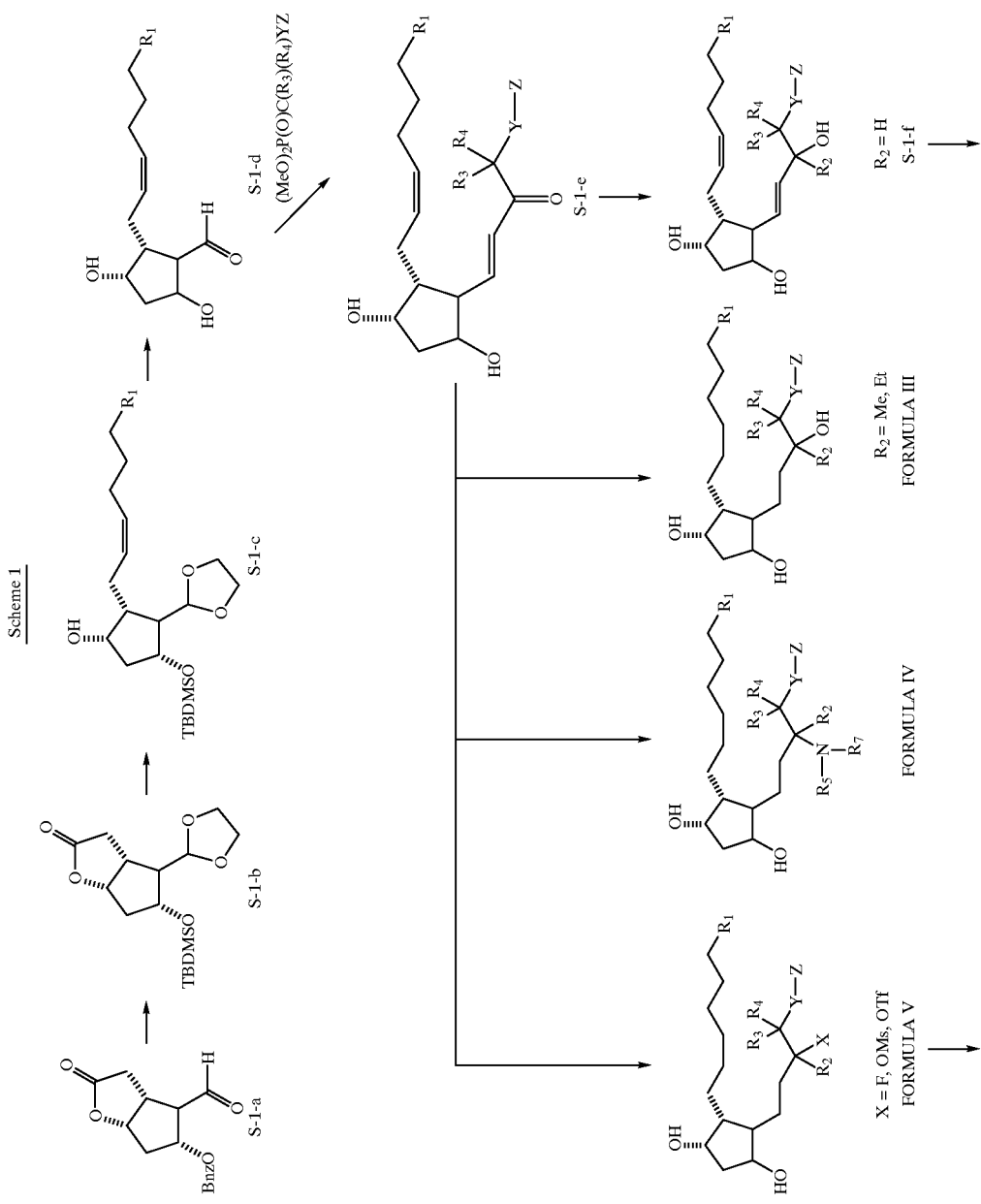

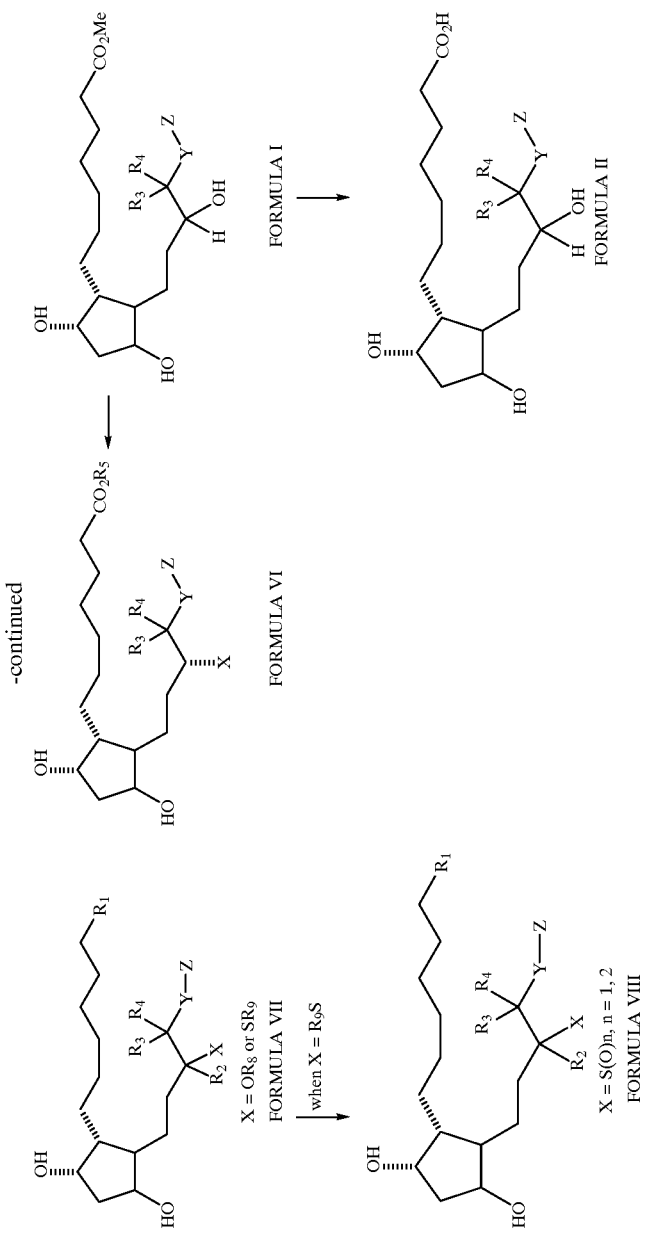

In Scheme 1, $R_1$, $R_2$, $R_3$, $R_4$, X, Y, and Z are as defined above. The Corey Lactone (S1a) depicted as starting material for Scheme 1 is commercially available (such as from Sumitomo Chemical or Cayman Chemical).

Compounds depicted by S1f are available from compounds of the type depicted by S1e via standard reduction reactions. Compounds depicted by Formula I are available from compounds of S1f via simultaneous saturation of the double bonds of S1f. Compounds depicted by Formula I are exemplified in Examples 2, 4, 5, 7, 9, 11, 13, 16, 18, 20, 22, 24, 26, and 28. Compounds depicted by Formula II are prepared through a simple deesterification protocol of the compounds of Formula I. Compounds depicted by Formula II are exemplified in Examples 1, 3, 6, 8, 10, 12, 14, 15, 17, 19, 21, 23, 25, 27, and 29. Compounds depicted by Formula III can be prepared from compounds such of S1e via the addition of a carbon nucleophile followed by saturation and saponification. Compounds depicted by Formula III are exemplified in Examples 43 and 44. Compounds depicted by Formula IV can be prepared via imine formation followed by imine reduction, N-alkylation, hydrogenation, and saponification. Additional compounds depicted by Formula IV can be prepared via imine formation, as previously mentioned, followed by nucleophilic addition to the resulting imine followed by double bond saturation and saponification. Compounds depicted by Formula IV are exemplified in Examples 48, 49, and 50.

Compounds depicted by Formula V and Formula VII can be prepared through dihydroxyl protection of compounds of S1e followed by standard nucleophilic reduction of the ketone. The resulting free alcohol can be activated and displaced with nucleophiles such as, but not limited to, fluoride, alkoxide or sulfide to give compounds depicted by Formula V or Formula VII. Compounds depicted by Formula V are exemplified in Examples 36, 37, and 38. Compounds depicted by Formula VII are exemplified in Examples 39, 40, 41, 42, and 45. Compounds depicted by Formula VIII are prepared by the selective oxidation of compounds of Formula VII with the proviso that X must be sulfur. Compounds depicted by Formula VIII are exemplified in Examples 46 and 47. Compounds of the type depicted by Formula VI can be prepared from either compounds of Formula I or Formula II (compounds depicted by Formula II may require carboxylate activation) through nucleophilic addition to an activated carboxylate to produce an amide or new ester linkage to give the resulting hydroxamic acid, sulfonamide, or ester. Compounds depicted by Formula VI are exemplified in Examples 30–35.

The following non-limiting examples illustrate the compounds, compositions, and uses of the present invention.

EXAMPLES

Compounds are analyzed using $^1$H and $^{13}$C NMR, Elemental analysis, mass spectra, high resolution mass spectra and/or IR spectra as appropriate.

Typically, inert solvents are used, preferably in dried form. For example, tetrahydrofuran (THF) is distilled from sodium and benzophenone, diisopropylamine is distilled from calcium hydride and all other solvents are purchased as the appropriate grade. Chromatography is performed on silica gel (70–230 mesh; Aldrich) or (230–400 mesh; Merck) as appropriate. Thin layer chromatography analysis is performed on glass mounted silica gel plates (200–300 mesh; Baker) and visualized using UV, 5% phosphomolybdic acid in EtOH, potassium permanganate in water, iodine, p-anisaldehyde in ethanol, or ammonium molybdate/cerric sulfate in 10% aqueous $H_2SO_4$.

Example 1

Preparation of 13,14-dihydro-17-(3-fluorophenyl)-17-trinor-prostaglandin $F_{1\alpha}$

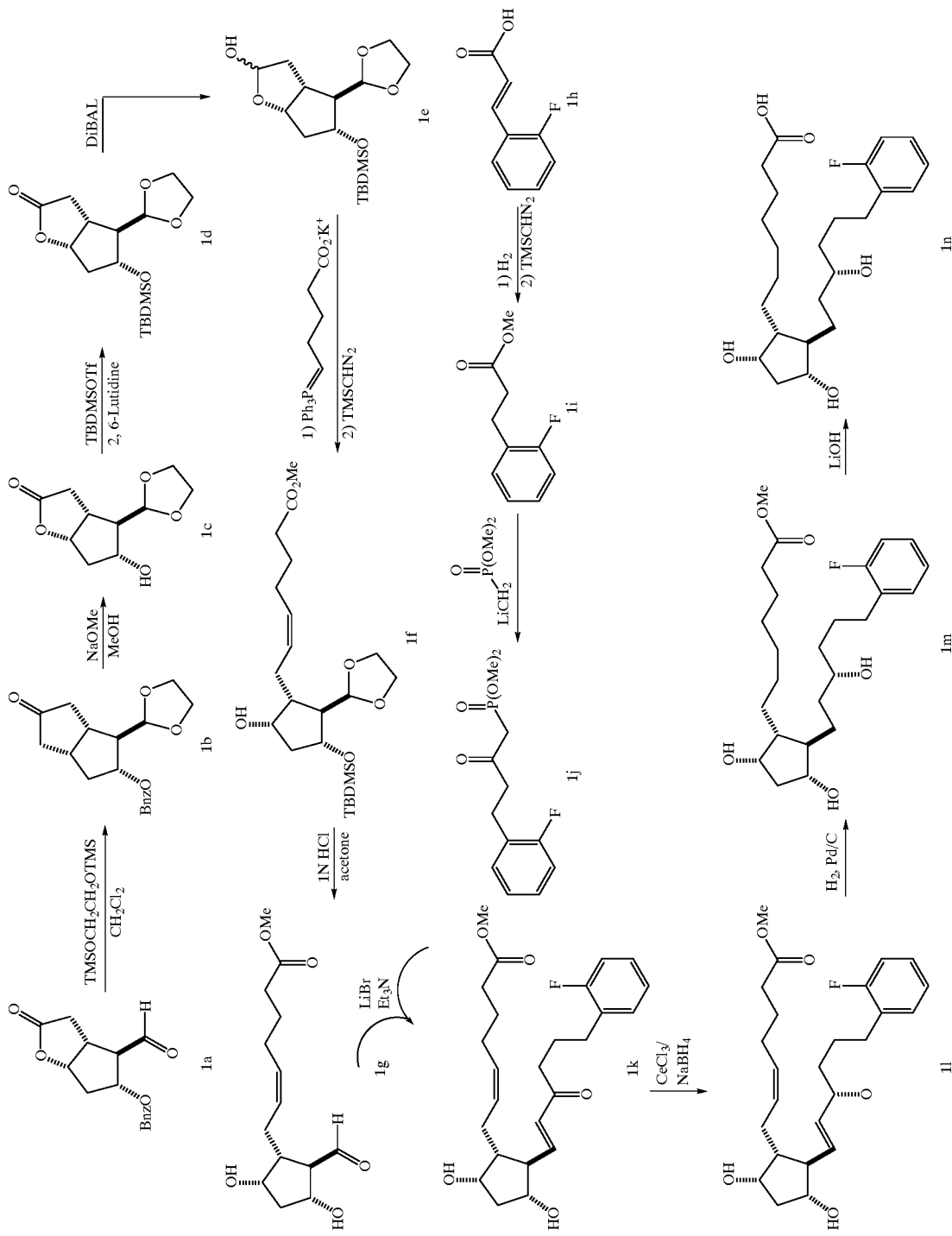

a. 7-benzoyloxy-6-(2,5-dioxolanyl)-2-oxabicyclo[3.3.0]octan-3-one (1b):

In a round-bottomed flask equipped with a magnetic stir bar is placed 1,2-bis(trimethylsilyloxy)ethane (1.3 equiv.) in methylene chloride containing trimethysilyltrifluoromethanesulfonate (1 mL) at −78° C. To this is added, within 20 minutes, a solution of 1a (1 equiv) in $CH_2Cl_2$. The reaction is stirred for 1 hour at −78° C. and then slowly warmed to 25° C. for 1 hour. The reaction is quenched at 0° C. with water, extracted with $CH_2Cl_2$, dried over $MgSO_4$, and concentrated in vacuo to give crude 1b.

b. 6-(2,5-dioxolanyl)-7-hydroxy-2-oxabicyclo[3.3.0]octan-3-one (1c):

To a well stirred solution of crude 1b (1 equiv) in methanol at 0° C. is added a suspension of sodium methoxide (1.2 equiv) in MeOH. The reaction stirred at 0° C. for 1 hour and then warmed to 25° C. for 1 hour. The reaction is neutralized with acidic ion exchange resin which is washed thoroughly with MeOH. The filtrate is concentrated in vacuo to give a syrup which is subjected to flash chromatography on silica gel eluting with 4:1 hexane:ethyl acetate and 2% MeOH in $CH_2Cl_2$ to give 1c as a yellow syrup.

c. 6-(2,5dioxolanyl)-2-oxa-7-(1,1,2,2-tetramethyl-1-silapropoxy) bicyclo[3.3.0]octan-3-one (1d):

In a round-bottomed flask with a magnetic stir bar, is stirred a solution of 1c (1 equiv) in $CH_2Cl_2$. To this solution is added dropwise at −78° C. 2,6-lutidine (1.9 equiv) followed by TBDMSOTf (1.8 eq). The reaction stirred for 30 minutes at −78° C. and then warmed to 25° C. overnight. The reaction is quenched with water. The organic layer is washed with water, dried over $MgSO_4$, and concentrated in vacuo to give a yellow oil which is subjected to flash chromatography on silica gel eluting with hexanes then 1% MeOH in $CH_2Cl_2$. The product is then washed with 1N HCl, 0.1N HCl, water, and brine to give 1d.

d. 6-(2,5dioxolanyl)-2-oxa-7-(1,1,2,2-tetramethyl-1-silapropoxy) bicyclo[3.3.0]octan-2-ol (1e):

In a round-bottomed flask with a magnetic stir bar, is stirred a solution of 1d (1 equiv) in dry toluene. To this solution, at −78° C., is slowly added DIBAL (1.24 equiv). The reaction mixture is stirred for 2 hours and then warmed to 0° C. Saturated $NH_4Cl$ is added to the reaction mixture which is then slowly warmed to 25° C. Diluted with water, the insoluble precipitate is removed by suction filtration and the solid is washed with EtOAc. The liquid phase is extracted with EtOAc and the combined organic phase is dried over $MgSO_4$ and concentrated in vacuo to give a yellow syrup. The product, 1e, must either be used immediately or stored at −70° C. overnight.

e. methyl 7-(5-(2,5-dioxolanyl)-2-hydroxy-4-(1,1,2,2-tetramethyl-(1-silapropoxy)cyclopentyl)hept-5-enoate (1f):

To a suspension of (4-carboxybutyl)triphenylphosphonium bromide (2.2 equiv) in THF at 0° C. under $N_2$ is added dropwise a solution of KHMDS (4.4 equiv). The resulting deep orange color reaction mixture is stirred for 1 hour at 25° C. To the reaction mixture above at −78° C. is added a solution of 1e (1 equiv) in THF. The reaction mixture is allowed to warm to 25° C. overnight. The reaction is quenched with water at 0° C. and the pH is adjusted to 3.5–4.0 with 1N HCl. The water phase is extracted with EtOAc and the combined organic phase is dried over $MgSO_4$ and is concentrated in vacuo to give a reddish-brown syrup containing crude acid. To a well stirred solution of crude acid in ether and MeOH at 0° C. is added TMS-diazomethane until a yellow color persists. The addition of 1 drop of glacial acetic acid, and thin layer chromatography verifies the reaction has gone to completion. The reaction solution is concentrated in vacuo and purified via flash chromatography on silica gel eluting with 30% EtOAc in hexanes yielding 1f.

f. methyl 7-(2,4-dihydroxy-5-formyl-cyclopentyl)hept-5-enoate (1g):

In a round-bottomed flask with a magnetic stir bar is placed an amount of the ketal, 1f. To this flask is added a sufficient amount of a mixture of 2 parts acetone to 1 part 1N HCl to bring the ketal completely into solution. This material is stirred until, by TLC, the starting material is consumed, typically overnight. The crude mixture, containing the product 1g, is extracted with ether, and the ether extract re-esterified in situ with, preferably, TMS-diazomethane. The organic extracts were concentrated under reduced pressure at 0° C. and used immediately without further purification.

g. Methyl 3-(2-fluorophenyl)propionate (1i):

In a Parr vessel is placed 2-fluorocinnamic acid (1h) (1.0 equiv) and palladium on carbon in a 1/1 methanol/ethyl acetate solution. The heterogeneous solution is placed on a Parr shaker and treated with hydrogen (50 psi) until uptake has ceased. The mixture is filtered through Celite and concentrated under reduced pressure. The residue is taken up in diethyl ether and treated with diazomethane until a yellow color persists. The solution is concentrated under reduced pressure to give the crude methyl ester. Purification is effected by column chromatography on silica gel (hexane/ethyl acetate 5/1) to yield Methyl 3-(2-fluorophenyl) propionate (1i) in quantitative yield.

h. Dimethyl-4-(2-fluorophenyl)-2-oxo-butylphosphonate (1j):

In a flame-diried, round-bottomed flask equipped with a stir bar and thermometer is placed dimethylmethyl phosphonate (1.0 equiv.) in anhydrous THF. The solution is cooled to −78° C. and treated with n-butyllithium (1.05 equiv.). The reaction mixture is allowed to stir for 15 minutes. To this solution is added methyl-3-(2-fluorophenyl) propionate (1.1 equiv.) in anhydrous THF. The mixture is allowed to warm to room temperature over the next 6 hours. The mixture is treated with a saturated solution of ammonium chloride and extracted with $CH_2Cl_2$. The organic layer is washed with water followed by brine. The combined aqueous layers are back extracted with $CH_2Cl_2$ and the organic layers combined, dried over anhydrous $MgSO_4$, filtered, and concentrated under reduced pressure. Purification is effected by silica gel column chromatography (hexane/ethyl acetate/2-propanol 45/50/5 to hexane/ethyl acetate/2-propanol 40/50/10) to yield 1.34 g (70%) of dimethyl-4-(2-fluorophenyl)-2-oxo-butylphosphonate (1j) as an oil.

i. 17-(2-fluorophenyl)-17-trinor-15-oxo-prostaglandin $F_{2\alpha}$ methyl ester (1k):

In a flame-dried, round-bottomed flask equipped with a magnetic stirbar is placed dimethyl-4-(2-fluorophenyl)-2-oxo-butylphosphonate (1j) (1.43 equiv) in DME and water. To this solution is added lithium bromide (1.65 equiv), triethylamine (1.65 equiv), and methyl 7-(2-formyl-3,5-dihydroxycyclopentyl)hept-5-enoate (1g) (1.0 equiv). The solution is stirred at room temperature for 48 hours. At this point additional triethylamine and water is added and the solution is stirred for an additional hour. The solution is poured into brine and extracted with 3 portions of ethyl acetate. The organic layers are combined, dried over anhydrous $MgSO_4$, filtered, and concentrated under reduced pressure. Purification is effected by silica gel column chromatography (dichloromethane/methanol 19/1) to give 17-

(2-fluorophenyl)-17-trinor-15-oxo-prostaglandin $F_{2\alpha}$ methyl ester (1k) as an oil.

j. 15-(R,S)-17-(2-fluorophenyl)-17-trinor-prostaglandin $F_{2\alpha}$ methyl ester (1l):

In a flame-dried round-bottomed flask equipped with a stir bar is placed 17-(2-fluorophenyl)-17-trinor-15-oxo-prostaglandin $F_{2\alpha}$ methyl ester (1k) (1.0 equiv), cerium trichloride (1.05 equiv) in methanol. The solution is stirred at room temperature for 5 minutes. The solution is cooled to −10° C. and sodium borohydride (1.02 equiv.) in methanol is added. The solution is stirred at −10° C. for 3 hours. The mixture is treated with water and the pH brought to 6–7 with 1N hydrochloric acid. The mixture is extracted twice with ethyl acetate, and the organic layers combined, dried over anhydrous $MgSO_4$, filtered and concentrated under reduced pressure. Purification was effected by silica gel column chromatography (3% methanol in dichloromethane to 5% methanol in dichloromethane) to give (43%) of the 15 (R) epimer and (19.6%) of the 15 (S) epimer as colorless oils.

k. 13,14-dihydro-17-(2-fluorophenyl)-17-trinor-prostaglandin $F_{1\alpha}$ methyl ester (1m):

In a flame-dried round-bottomed flask equipped with a stir bar was placed 17-(2-fluorophenyl)-17-trinor-prostaglandin $F_{2\alpha}$ methyl ester (1l) (1.0 equiv.) and palladium on carbon in ethyl acetate (3 mL). The heterogeneous mixture is treated with hydrogen via a balloon for 18 hours. The mixture is filtered through Celite and concentrated under reduced pressure to give a quantitative yield 13,14-dihydro-17-(2-fluorophenyl)-17-trinor-prostaglandin $F_{1\alpha}$ methyl ester (1m).

l. 13,14-dihydro-17-(2-fluorophenyl)-17-trinor-prostaglandin $F_{1\alpha}$ methyl ester (1n):

In a round-bottomed flask equipped with a stir bar is placed 13,14-dihydro-17-(2-fluorophenyl)-17-trinor-prostaglandin $F_{1\alpha}$ methyl ester (1m) (1.0 equiv) and lithium hydroxide monohydrate (1.8 equiv) in a 50/50 THF water solution. The mixture is stirred at room temperature for 6 hours and then diluted with water and acidified to pH 2–3 with 1N HCl. The aqueous phase is extracted 3 times with ethyl acetate and the organic layers combined. The combined organics were dried over anhydrous $MgSO_4$, filtered, and concentrated under reduced pressure to yield the crude acid. Purification was effected by HPLC to yield (41%) of an analytical sample. Utilizing substantially the method of Example 1 (and using the appropriate starting materials), the following subject compounds of Examples 2–29 are obtained.

Example 2

13,14-dihydro-17-(2,4difluorophenyl)-17-trinor prostaglandin $F_{1\alpha}$ methyl ester

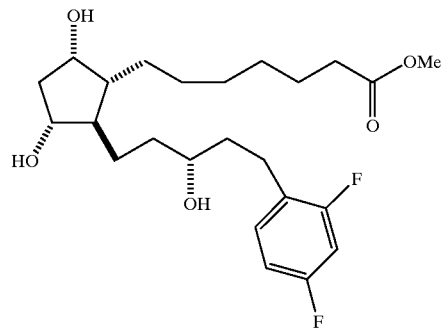

Example 3

13,14-dihydro-17-(2,4difluorophenyl)-17-trinor prostaglandin $F_{1\alpha}$

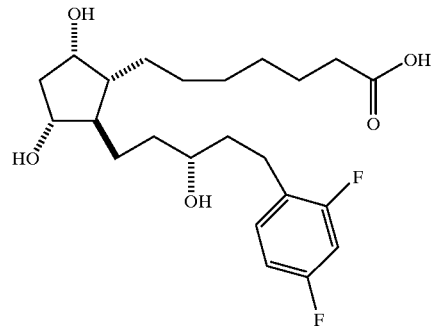

Example 4

13,14-dihydro-17-(2-fluorophenyl)-17-trinor prostaglandin $F_{1\alpha}$ methyl ester

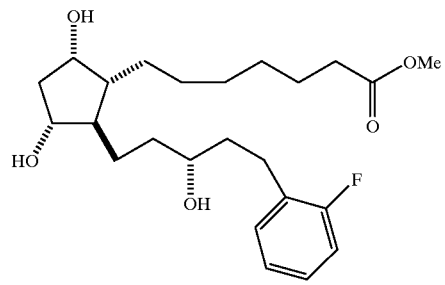

Example 5

13,14-dihydro-17-(3-fluorophenyl)-17-trinor prostaglandin $F_{1\alpha}$ methyl ester

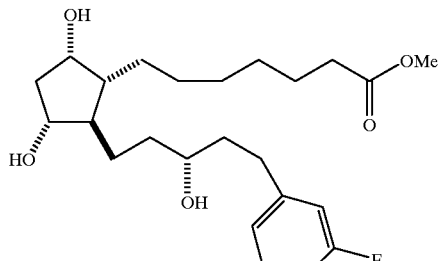

Example 6

13,14-dihydro-17-(3-fluorophenyl-17-trinor prostaglandin $F_{1\alpha}$

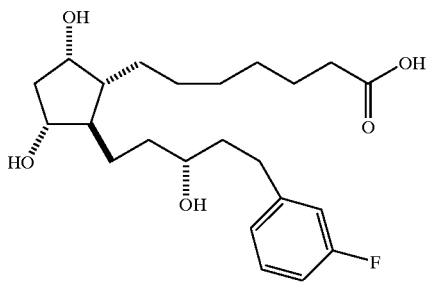

Example 7

13,14-dihydro-17-(4-fluorophenyl)-17-trinor prostaglandin $F_{1\alpha}$ methyl ester

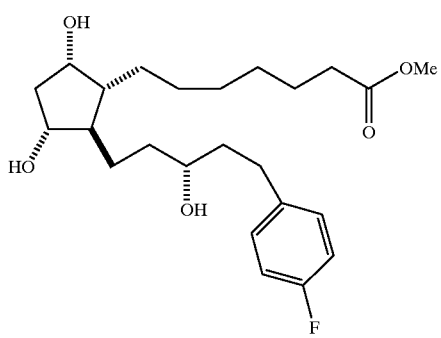

Example 8

13,14-dihydro-17-(4-fluorophenyl)-17-trinor prostaglandin $F_{1\alpha}$

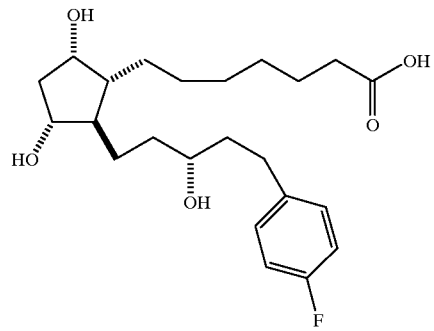

Example 9

13,14-dihydro-17-(2-methoxyphenyl)-17-trinor prostaglandin $F_{1\alpha}$ methyl ester

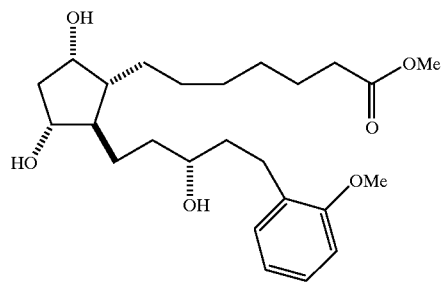

Example 10

13,14-dihydro-17-(2-methoxyphenyl)-17-trinor prostaglandin $F_{1\alpha}$

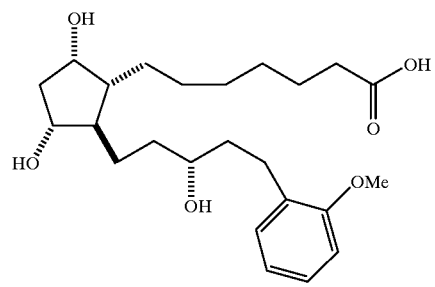

Example 11

13,14-dihydro-17-(3-methoxyphenyl)-17-trinor prostaglandin F$_{1\alpha}$ methyl ester

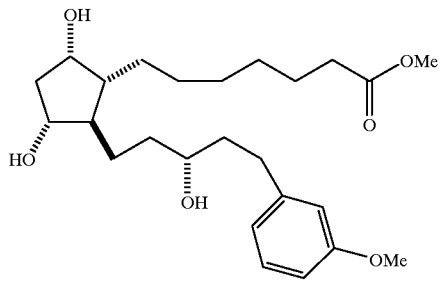

Example 12

13,14-dihydro-17-(3-methoxyphenyl)-17-trinor prostaglandin F$_{1\alpha}$

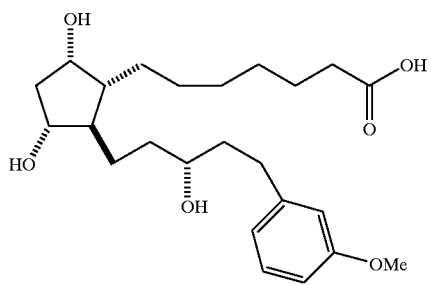

Example 13

13,14-dihydro-17-(4-methoxyphenyl)-17-trinor prostaglandin F$_{1\alpha}$ methyl ester

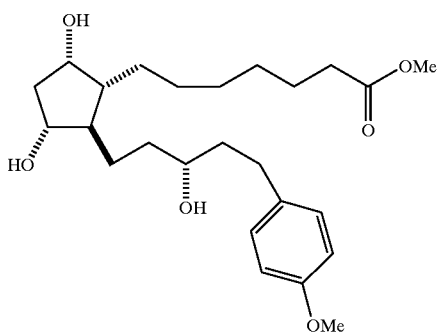

Example 14

13,14-dihydro-17-(4-methoxyphenyl)-17-trinor prostaglandin F$_{1\alpha}$

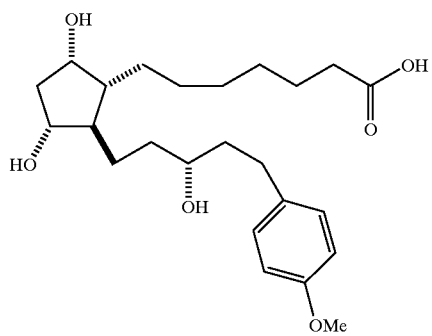

Example 15

13,14-dihydro-17-(3,5-difluorophenyl)-17-trinor prostaglandin F$_{1\alpha}$

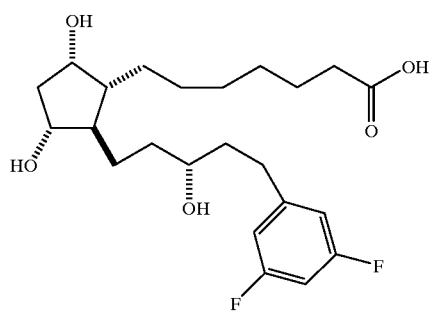

Example 16

13,14-dihydro-18-(2-thienyl)-18-dinor prostaglandin F$_{1\alpha}$ methyl ester

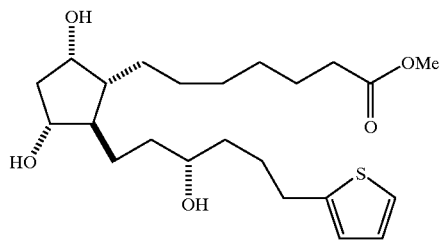

Example 17

13,14-dihydro-18-(2-thienyl)-18-dinor prostaglandin F$_{1\alpha}$

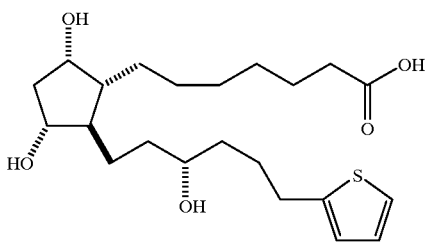

Example 18

13,14-dihydro-17-((2-trifluoromethyl)phenyl)-17-trinor prostaglandin F$_{1\alpha}$ methyl ester

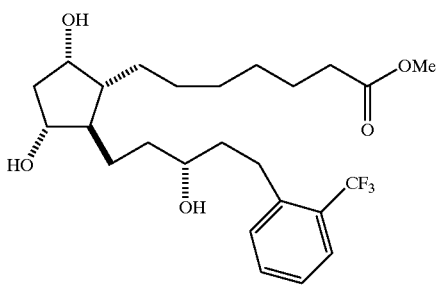

Example 19

13,14-dihydro-17-((2-trifluoromethyl)phenyl)-17-trinor prostaglandin F$_{1\alpha}$

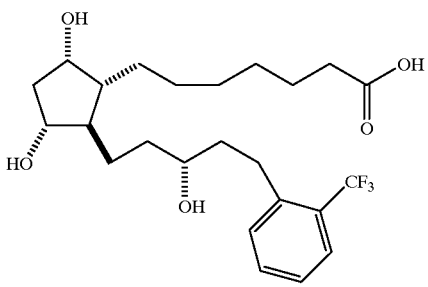

Example 20

13,14-dihydro-17-((3-trifluoromethyl)phenyl)-17-trinor prostaglandin F$_{1\alpha}$ methyl ester

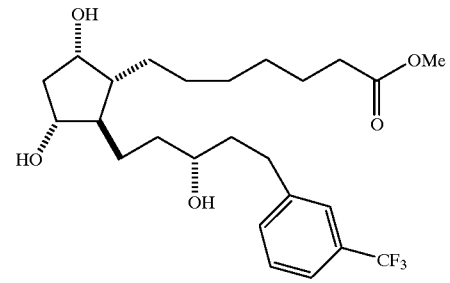

Example 21

13,14-dihydro-17-((3-trifluoromethyl)phenyl)-17trinor prostaglandin F$_{1\alpha}$

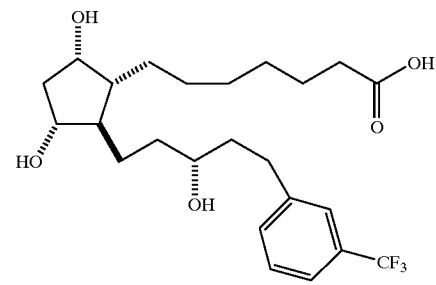

Example 22

13,14-dihydro-17-((4-trifluoromethyl)phenyl)-17-trinor prostaglandin F$_{1\alpha}$ methyl ester

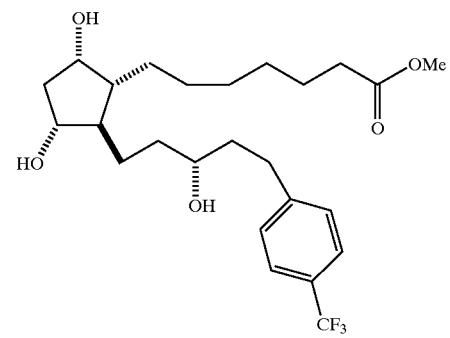

Example 23

13,14-dihydro-17-((4-trifluoromethyl)phenyl)-17-trinor prostaglandin $F_{1\alpha}$

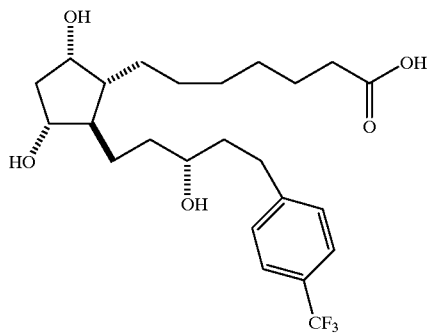

Example 24

13,14-dihydro-17-(2-methylphenyl-17-trinor prostaglandin $F_{1\alpha}$ methyl ester

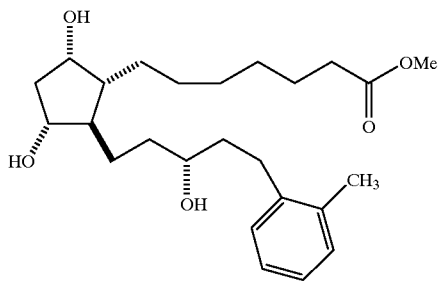

Example 25

13,14-dihydro-17-(2-methylphenyl)-17-trinor prostaglandin $F_{1\alpha}$

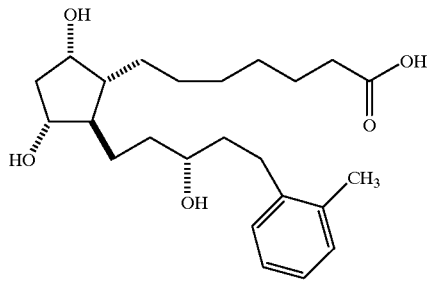

Example 26

13,14-dihydro-17-(3-methylphenyl)-17-trinor prostaglandin $F_{1\alpha}$ methyl ester

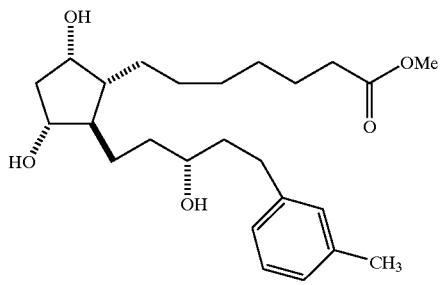

Example 27

13,14-dihydro-17-(3-methylphenyl)-17-trinor prostaglandin $F_{1\alpha}$

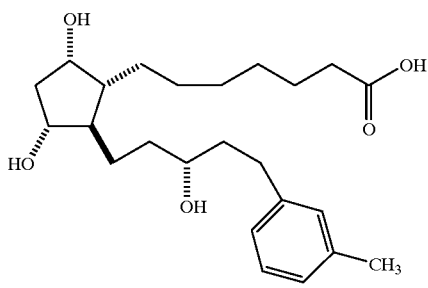

Example 28

13,14-dihydro-17-(4-methylphenyl)-17-trinor prostaglandin $F_{1\alpha}$ methyl ester

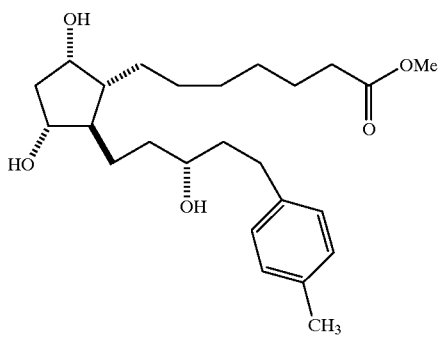

Example 29

13,14-dihydro-17-(4-methylphenyl)-17-trinor prostaglandin $F_{1\alpha}$

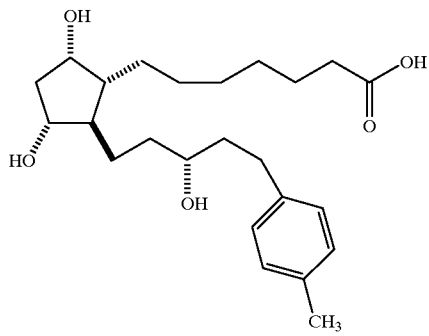

Example 30

13,14-dihydro-17-((3-trifluoromethyl)phenyl)-17-trinor prostaglandin $F_{1\alpha}$-1-hydroxamic acid

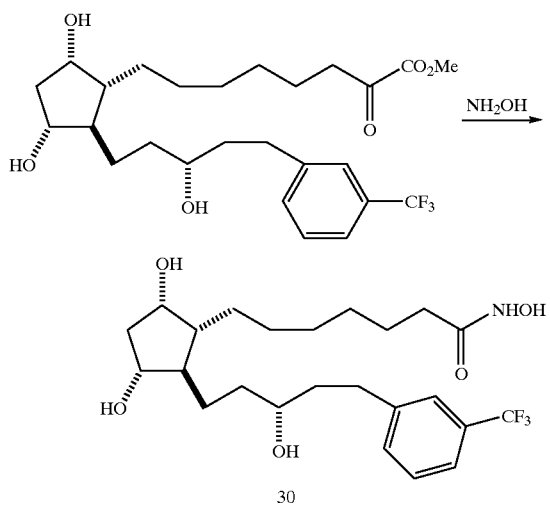

To a solution of 13,14-dihydro-17-(3-trifluoromethyl)-phenyl trinor prostaglandin $F_{1\alpha}$ methyl ester (Example 20) in methanol is added hydroxylamine in basic methanol (1.25 equiv.). The solution is stirred at room temperature for 18 hours. The solution is treated with 1N hydrochloric acid and extracted with ethyl acetate. The organic layer is washed with brine and dried over anhydrous magnesium sulfate, filtered and concentrated under reduced pressure. The residue is purified by HPLC to yield 13,14-dihydro-17-((3-trifluoromethyl)phenyl)-17-trinor prostaglandin $F_{1\alpha}$-1-hydroxamic acid.

Utilizing substantially the method of Example 30 (and using the appropriate ester), the following subject compounds of Examples 31 and 32 are obtained.

Example 31

13,14-dihydro-17-(2-methoxyphenyl)-17-trinor prostaglandin $F_{1\alpha}$-1-hydroxamic acid

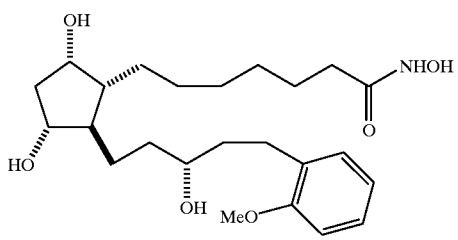

Example 32

13,14-dihydro-18-(2-thienyl)-dinor prostaglandin $F_{1\alpha}$-1-hydroxamic acid

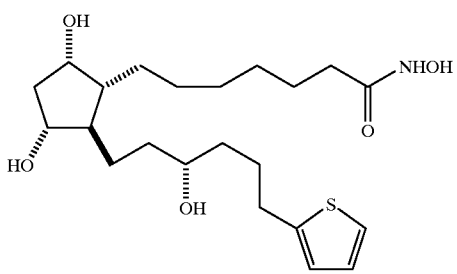

Example 33

13,14-dihydro-17-((4-trifluoromethyl)phenyl)-17-trinor prostaglandin $F_{1\alpha}$-1-sulfonamide

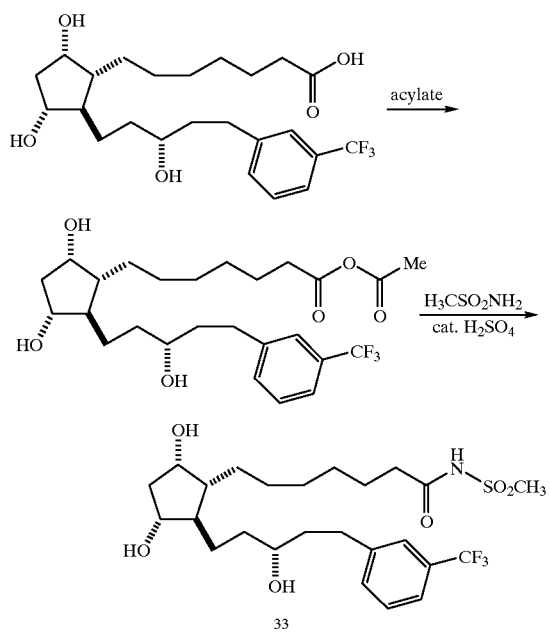

Example 23 is converted to the anhydride followed by treatment with methanesulfonylamide as disclosed in A. D. Kemp and H. Stephen, *J. Chem. Soc.* (1948) p. 110.

Utilizing substantially the method of Example 33 (and using the appropriate acid), the following subject compounds of Examples 34 and 35 are obtained.

Example 34

13,14-dihydro-17-(4-methylphenyl)-17-trinor prostaglandin $F_{1\alpha}$-1-sulfonamide

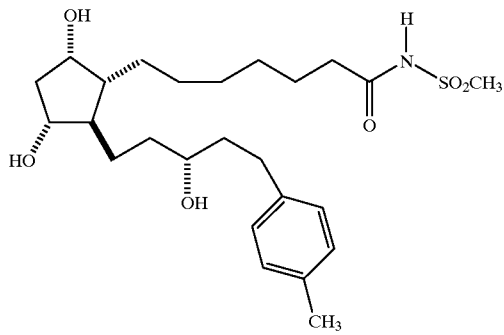

Example 35

13,14-dihydro-17-(2,4difluorophenyl)-17-trinor prostaglandin $F_{1\alpha}$-1-sulfonamide

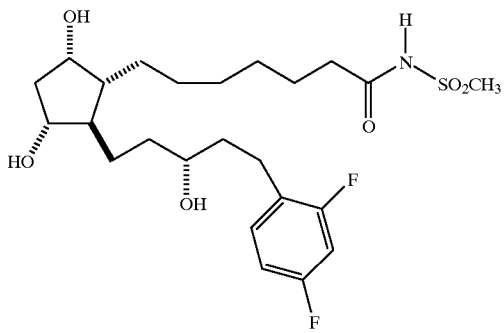

Example 36

13,14-dihydro-15-fluoro-17-(3-methylphenyl)-17-trinor prostaglandin $F_{1\alpha}$

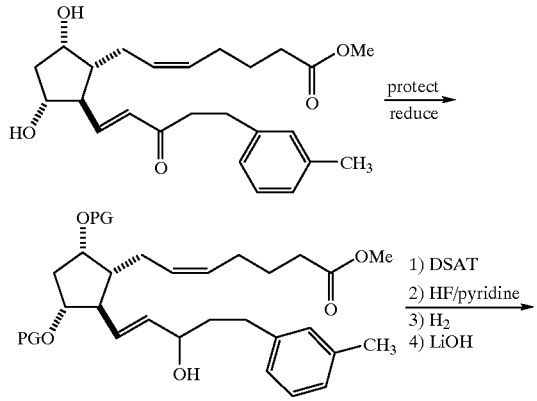

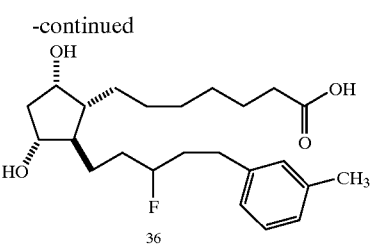

The precursor to Example 27 corresponding to 1k from Example 1 is protected and reduced to give the 9,11-protected bis ether. The resulting compound is treated with diethylaminosulfur trifluoride (DSAT) (as disclosed in the following references: *Org. React.* Vol. 35 (1988) p. 513; *J. Org. Chem.* Vol. 40 (1975) p. 574; and references cited therein) to give 13,14-dihydro-15-fluoro-17-(3-methylphenyl)-17-trinor prostaglandin $F_{1\alpha}$ after the appropriate transformation as described in Example 1.

Examples 37 and 38 are prepared in a manner substantially similar to Example 36 using the appropriate intermediate corresponding to 1k (from Example 5 and Example 25 respectively) in Example 1 followed by standard esterification with the appropriate alcohol.

Example 37

13,14-dihydro-15-fluoro-17-(3-fluorophenyl)-17-trinor prostaglandin $F_{1\alpha}$ ethyl ester

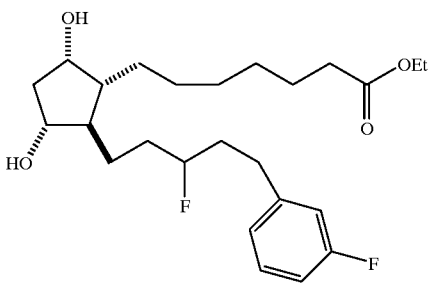

Example 38

13,14-dihydro-15-fluoro-17-(2-methylphenyl)-17-trinor prostaglandin $F_{1\alpha}$ isopropyl ester

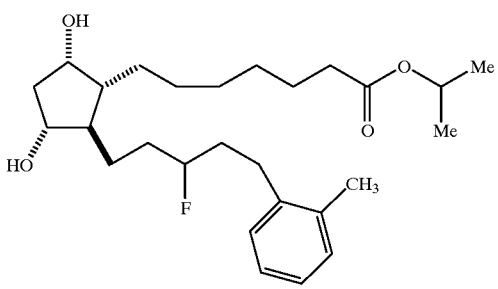

Example 39

13,14-dihydro-15-methylthio-17-((4-trifluoromethyl)phenyl)-17-trinor prostaglandin $F_{1\alpha}$

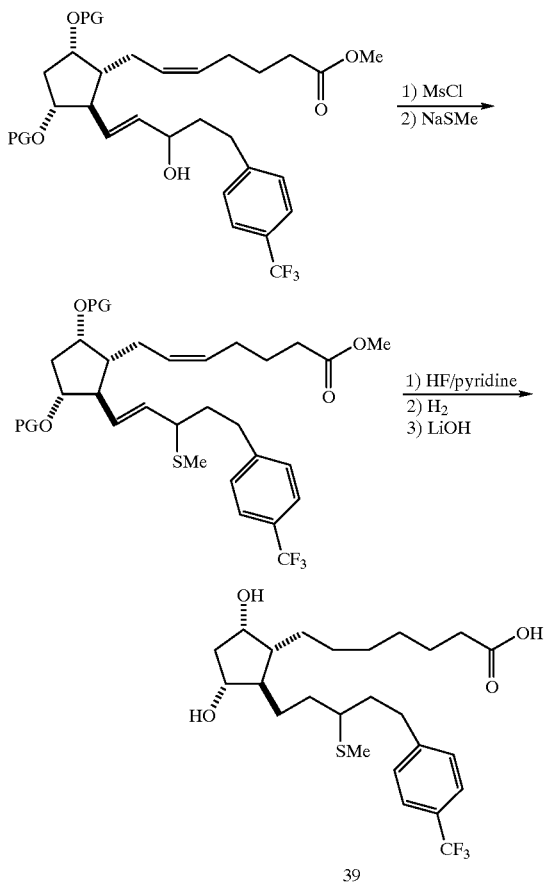

The precursor to Example 23 corresponding to 1k from Example 1 is protected and reduced to give the 9,11-protected bis ether. This compound is treated with methanesulfonyl chloride (1.2 equiv) and base (1.2 equiv) (as disclosed in the following references: *J.C.S. Chem. Comm.* (1975) p. 658; *Tetrahedron Lett.* (1975) p. 3183; and references cited therein) to generate the intermediate mesylate, which is then treated immediately with nucleophiles (sodium thiomethoxide) (as disclosed in *Tetrahedron Lett.* Vol. 23 (1982) p. 3463 and references cited therein.) to give the protected thioalkyl ether. Subsequent transformation as described in Example 1 provides 13,14-dihydro-15-methylthio-17-((4-trifluoromethyl)phenyl)-17-trinor prostaglandin $F_{1\alpha}$.

Example 40 is prepared in a manner substantially similar to Example 39 (from a precursor corresponding to 1k from Example 7) followed by conversion to the hydroxamic acid as shown in Example 30.

Example 40

13,14-dihydro-15-methylthio-17-(4-fluorophenyl)-17-trinor prostaglandin $F_{1\alpha}$ hydroxamic acid

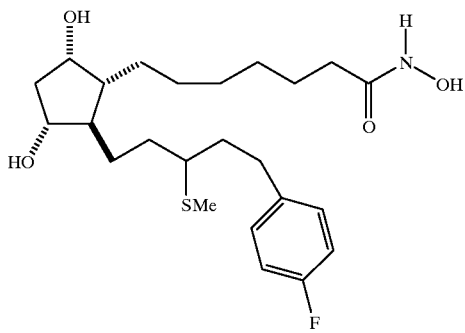

Example 41 is prepared in a substantially similar manner as Example 39 (from a precursor corresponding to 1k from Example 21) followed by conversion to the sulfonamide as shown in Example 33.

Example 41

13,14-dihydro-15-methylthio-17-((3-trifluoromethyl)phenyl)-17-trinor prostaglandin $F_{1\alpha}$-sulfonamide

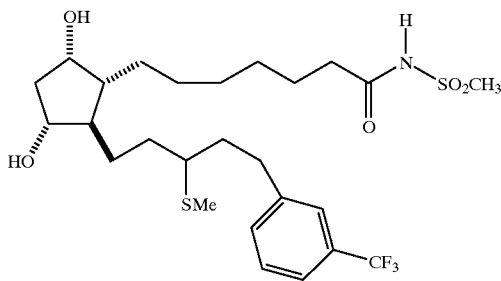

Example 42

13,14-dihydro-15-ethoxy-17-((2-trifluoromethyl)phenyl)-17-trinor prostaglandin $F_{1\alpha}$

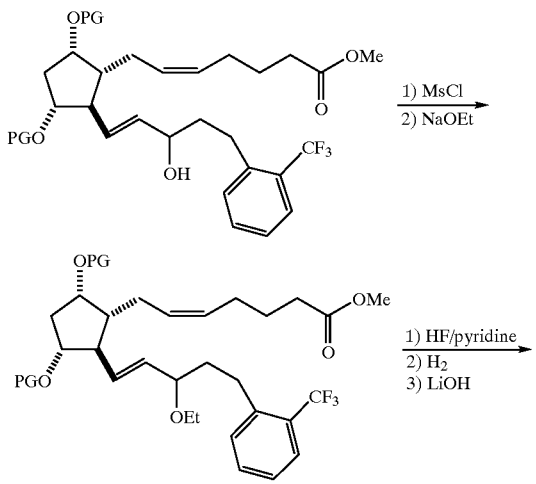

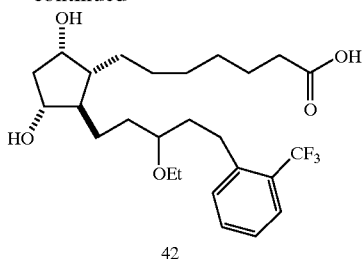

42

The precursor to Example 19 corresponding to 1k from Example 1 is protected and reduced to give the 9,11-protected bis ether. This compound is treated with methanesulfonyl chloride (1.2 equiv.) and base (1.2 equiv.) (as disclosed in the following references: *J.C.S. Chem. Comm.* (1975) p. 658; *Tetrahedron Lett.* (1975) p. 3183; and references cited therein.) to generate the intermediate mesylate, which is then treated immediately with sodium ethoxide to give the protected alkyl ether. Subsequent transformation as described in Example 1 provides 13,14-dihydro-15-ethoxy-17-((2-trifluoromethyl)phenyl)-17-trinor prostaglandin $F_{1\alpha}$.

Example 43

13,14-dihydro-15-ethyl-18-(2-thienyl)-18-dinor prostaglandin $F_{1\alpha}$

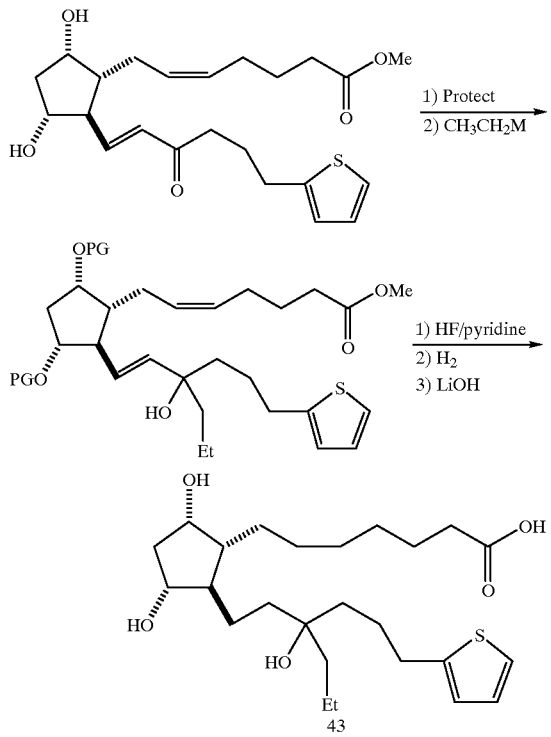

The precursor to Example 17 corresponding to 1k from Example 1 is protected and reduced to give the 9,11-protected bis ether. The resulting protected diol is treated with one of a variety of carbon nucleophiles, such as ethyl magnesium bromide to give the resulting tertiary alcohol. Deprotection followed by the transformation outlined in Example 1 provides 13,14-dihydro-15-ethyl-18-(2-thienyl)-18-dinor prostaglandin $F_{1\alpha}$.

Utilizing substantially the method of Example 43 (and using the appropriate carbon nucleophile), the following subject compound of Example 44 is obtained.

Example 44

13,14-dihydro-15-methyl-17-(3,5-difluorophenyl)-17-trinor prostaglandin $F_{1\alpha}$

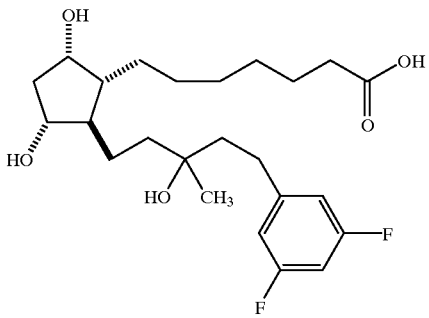

Example 45

13,14-dihydro-15-ethyl-15-methoxy-17-(4-methoxyphenyl)-17-trinor prostaglandin $F_{1\alpha}$

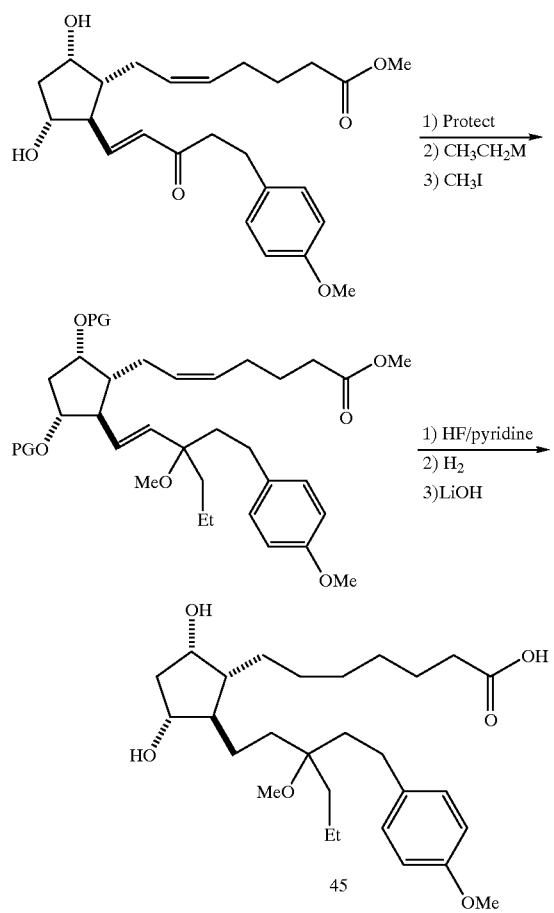

The compound of Example 45 is prepared by utilizing the protocol outlined in Example 43 (from the precursor corresponding to 1k for Example 13) followed by O-alkylation of the resulting $C_{15}$ alkoxide with a variety of alkyl halides (iodomethane in this example). This is followed by deprotection, hydrogenation, and saponificiation as outlined in Example 43 and Example 1 to give 13,14-dihydro-15-ethyl-15-methoxy-17-(4-methoxyphenyl)-17-trinor prostaglandin $F_{1\alpha}$

Example 46

13,14-dihydro-15-sulfonylmethyl-17-((4-trifluoromethyl)phenyl)-17-trinor prostaglandin $F_{1\alpha}$

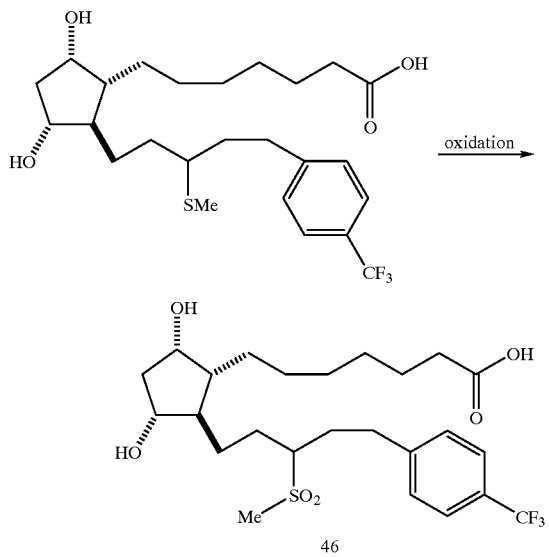

The thiomethyl ether of Example 39 is treated with the appropriate oxidizing agent as disclosed in the following references: *Tetrahedron Lett.* (1982) p. 3467; *Prostaglandins* Vol. 24 (1982) p. 801; *Tetrahedron Lett.* Vol. 23 (1982) p. 1023; and references cited therein.

Utilizing substantially the method of Example 46 (and using the appropriate thioether), the following subject compound of Example 47 is obtained.

Example 47

13,14-dihydro-15-sulfoxylmethyl-17-((4-trifluoromethyl)phenyl)-17-trinor prostaglandin $F_{1\alpha}$

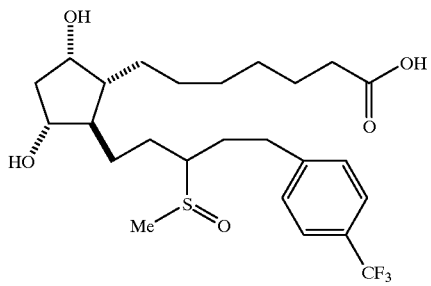

Example 48

13,14-dihydro-15-N-methylamino-17-(3-methoxyphenyl)-17-trinor prostaglandin $F_{1\alpha}$

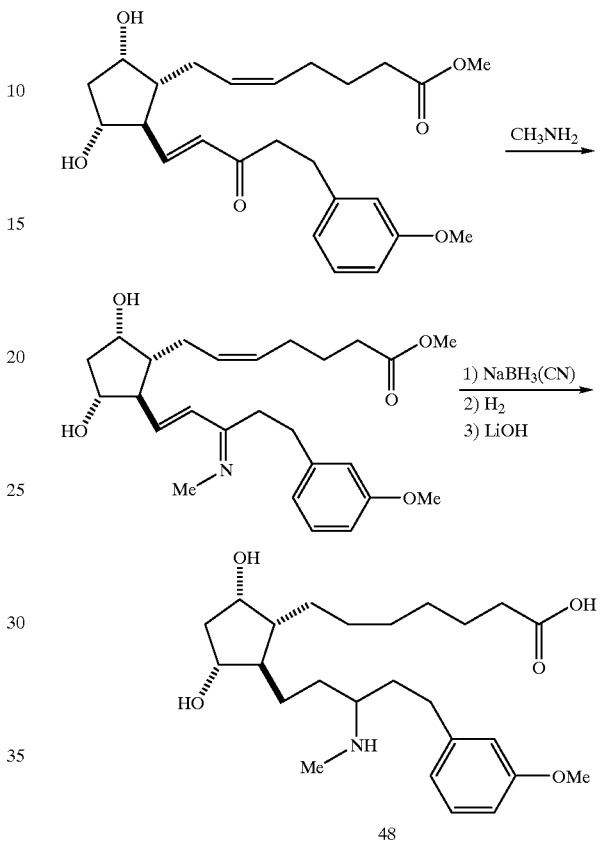

The intermediate of Example 12 corresponding to 1k is condensed with methyl amine followed by reduction with sodium cyanoborohydride to give 13,14-dihydro-15-N-methylamino-17-(3-methoxyphenyl)-17-trinor prostaglandin $F_{1\alpha}$, after saponification and deprotection.

Example 49

13,14-dihydro-15-N,N'-dimethylamino-17-(3-methoxyphenyl)-17-trinor prostaglandin $F_{1\alpha}$

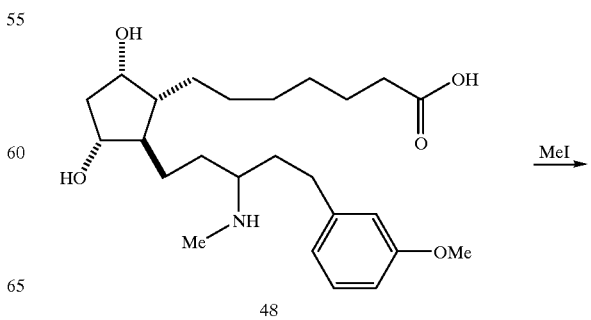

-continued

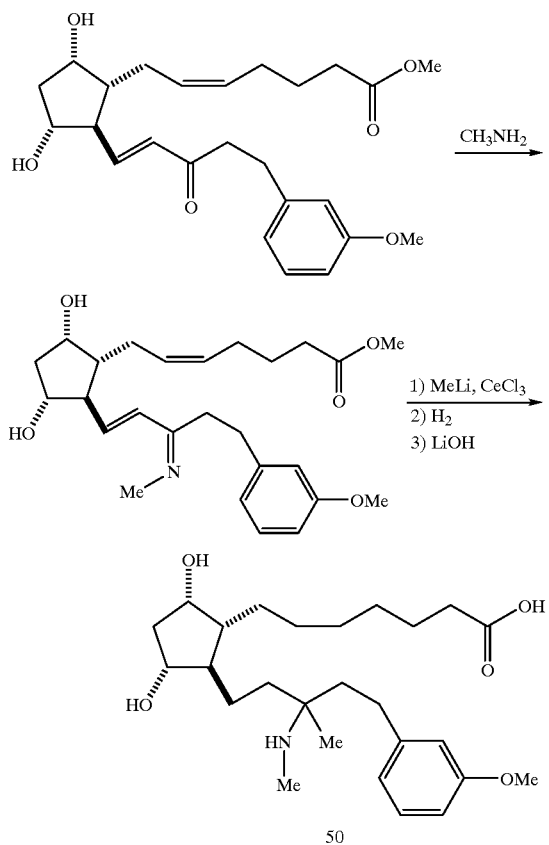

The compound of Example 49 is prepared from the compound of Example 48 by simple alkylation with iodomethane.

Example 50

13,14-dihydro-15-aminomethyl-15-methyl-17-(3-methoxyphenyl)-17-trinor prostaglandin $F_{1\alpha}$ The intermediate imine of Example 48 is treated with methylcerium (excess) (for examples of cerium-mediated nucleophilic additions see the following references: *J. Org. Chem.*, Vol. 49 (1984) p. 3904; *J. Am. Chem. Soc.*, Vol. 111 (1989) p. 4392; and references therein) to give 13,14-dihydro-15-aminomethyl-15-methyl-17-(3-methoxyphenyl)-17-trinor prostaglandin $F_{1\alpha}$ after hydrogenation and saponification as described in Example 1.

Compositions

Compositions of the subject invention comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

In addition to the compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a subject. The term "compatible", as used herein, means that the components of the composition are capable of being commingled with the compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the subject being treated.

Some examples of substances which can serve as pharmaceutically-acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragacanth; malt; gelatin; talc; solid lubricants, such as stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the Tweens®; wetting agents such as sodium lauryl sulfate; coloring agents; flavoring agents, excipients; tableting agents; stabilizers; antioxidants; preservatives; pyrogen-free water; isotonic saline; and phosphate buffer solutions.

The choice of a pharmaceutically-acceptable carrier to be used in conjunction with a compound is basically determined by the way the compound is to be administered. The compounds of the present invention may be administered systemically. Routes of administration include transdermal; oral; parenterally, including subcutaneous or intravenous injection; topical; and/or intranasal.

The appropriate amount of the compound to be used may be determined by routine experimentation with animal models. Such models include, but are not limited to the intact and ovariectomized rat models, the ferret, canine, and non human primate models as well as disuse models.

Preferred unit dosage forms for injection include sterile solutions of water, physiological saline, or mixtures thereof. The pH of said solutions should be adjusted to about 7.4. Suitable carriers for injection or surgical implants include hydrogels, controlled- or sustained release devises, polylactic acid, and collagen matrices.

Suitable pharmaceutically-acceptable carriers for topical application include those suited for use in lotions, creams, gels and the like. If the compound is to be administered perorally, the preferred unit dosage form is tablets, capsules and the like. The pharmaceutically-acceptable carriers suitable for the preparation of unit dosage forms for oral administration are well-known in the art. Their selection will depend on secondary considerations like taste, cost, and shelf stability, which are not critical for the purposes of the subject invention, and can be made without difficulty by those skilled in the art.

Methods of Use

The compounds of the present invention are useful in treating many medical disorders, including for example, ocular disorders, hypertension, fertility control, nasal congestion, neurogenic bladder disorder, gastrointestinal disorders, dermatological disorders, and osteoporosis.

The compounds of the present invention are useful in increasing bone volume and trabecular number through formation of new trabeculae, increasing bone mass while maintaining a normalized bone turnover rate, and formation of bone at the endosteal surface without removing bone from the existing cortex. Thus, these compounds are useful in the treatment and prevention of bone disorders.

The preferred routes of administration for treating bone disorders are transdermal and intranasal. Other preferred routes of administration include rectal, sublingual, and oral.

The dosage range of the compound for systemic administration is from about 0.01 to about 1000 μg/kg body weight, preferably from about 0.1 to about 100 μg/kg per body weight, most preferably from about 1 to about 50 μg/kg body weight per day. The transdermal dosages will be designed to attain similar serum or plasma levels, based upon techniques known to those skilled in the art of pharmacokinetics and transdermal formulations. Plasma levels for systemic administration are expected to be in the range of 0.01 to 100 nanograms/ml, more preferably from 0.05 to 50 ng/ml, and most preferably from 0.1 to 10 ng/ml. While these dosages are based upon a daily administration rate, weekly or monthly accumulated dosages may also be used to calculate the clinical requirements.

Dosages may be varied based on the patient being treated, the condition being treated, the severity of the condition being treated, the route of administration, etc. to achieve the desired effect.

The compounds of the present invention are also useful in decreasing intraocular pressure. Thus, these compounds are useful in the treatment of glaucoma. The preferred route of administration for treating glaucoma is topically.

Composition and Method Examples

The following non-limiting examples illustrate the subject invention. The following composition and method examples do not limit the invention, but provide guidance to the skilled artisan to prepare and use the compounds, compositions and methods of the invention. In each case other compounds within the invention may be substituted for the example compound shown below with similar results. The skilled practitioner will appreciate that the examples provide guidance and may be varied based on the condition being treated and the patient.

Example A

Pharmaceutical compositions in the form of tablets are prepared by conventional methods, such as mixing and direct compaction, formulated as follows:

| Ingredient | Quantity (mg per tablet) |
|---|---|
| Compound of Example 1 | 5 |
| Microcrystalline Cellulose | 100 |

-continued

| Ingredient | Quantity (mg per tablet) |
|---|---|
| Sodium Starch Glycollate | 30 |
| Magnesium Stearate | 3 |

When administered orally once daily, the above composition substantially increases bone volume in a patient suffering from osteoporosis.

Example B

Pharmaceutical compositions in liquid form are prepared by conventional methods, formulated as follows:

| Ingredient | Quantity |
|---|---|
| Compound of Example 1 | 5 mg |
| Phosphate buffered physiological saline | 10 mll |
| Methyl Paraben | 0.05 ml |

When 1.0 ml of the above composition is administered subcutaneously once daily, the above composition substantially increases bone volume in a patient suffering from osteoporosis.

Example C

Topical pharmaceutical compositions for lowering intraocular pressure are prepared by conventional methods and formulated as follows:

| Ingredient | Amount (wt %) |
|---|---|
| Compound of Example 38 | 0.004 |
| Dextran 70 | 0.1 |
| Hydroxypropyl methylcellulose | 0.3 |
| Sodium Chloride | 0.77 |
| Potassium chloride | 0.12 |
| Disodium EDTA (Edetate disodium) | 0.05 |
| Benzalkonium chloride | 0.01 |
| HCL and/or NaOH | pH 7.2–7.5 |
| Purified water | q.s. to 100% |

While particular embodiments of the subject invention have been described, it would be obvious to those skilled in the art that various changes and modifications to the compositions disclosed herein can be made without departing from the spirit and scope of the invention. It is intended to cover, in the appended claims, all such modifications that are within the scope of this invention.

What is claimed is:

1. A compound having the structure:

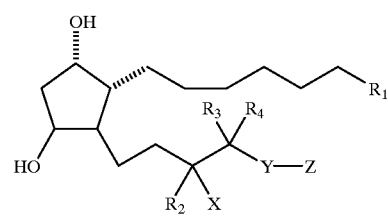

wherein
(a) $R_1$ is $CO_2H$, $C(O)NHOH$, $CO_2R_5$, $CH_2OH$, $S(O)_2R_5$, $C(O)NHR_5$, $C(O)NHS(O)_2R_5$, or tetrazole; wherein $R_5$ is alkyl, heteroalkyl, carbocyclic aliphatic ring, heterocyclic aliphatic ring, aromatic ring, or heteroaromatic ring;

(b) $R_2$ is H or lower alkyl;

(c) X is $NR_6R_7$, $OR_8$, $SR_9$, $S(O)R_9$, $S(O)_2R_9$, or F; wherein $R_6$, $R_7$, and $R_8$ are independently selected from the group consisting of H, acyl, alkyl, heteroalkyl, carbocyclic aliphatic ring, heterocyclic aliphatic ring, aromatic ring, and heteroaromatic ring; and wherein $R_9$ is alkyl, heteroalkyl, carbocyclic aliphatic ring, heterocyclic aliphatic ring, aromatic ring, or heteroaromatic ring;

(d) $R_3$ and $R_4$ are independently H, $CH_3$, $C_2H_5$, $OR_{10}$, $SR_{10}$, or OH, except that both $R_3$ and $R_4$ are not OH; wherein $R_{10}$ is alkyl, heteroalkyl, carbocyclic aliphatic ring, heterocyclic aliphatic ring, aromatic ring, or heteroaromatic ring, $R_{10}$ having from 1 to about 8 member atoms;

(e) Y is $(CH_2)_n$; n being an integer from 1 to about 3;

(f) Z is heterocyclic aliphatic ring, monocyclic heteroaromatic ring, or substituted phenyl when n is 2 or 3 wherein said phenyl substituents are selected from the group consisting of halo, cyano, heteroalkyl, haloalkyl, and phenyl; and Z is heterocyclic aliphatic ring or substituted phenyl when n is 1 wherein said phenyl substituents are selected from the group consisting of halo, cyano, heteroalkyl, haloalkyl, and phenyl; wherein heteroalkyl is a saturated or unsaturated chain containing carbon and at least one heteroatom; and any optical isomer, diasteroemer, enantiomer of the above structure, or a pharmaceutically-acceptable salt, or biohydrolyzable amide, ester, or imide thereof.

2. The compound according to claim 1 wherein $R_1$ is selected from the group consisting of $CO_2H$, $C(O)NHOH$, $CO_2CH_3$, $CO_2C_2H_5$, $CO_2C_3H_7$, $CO_2C_4H_9$, $CO_2C_3H_7O_2$, and $C(O)NHS(O)_2R_5$.

3. The compound according to claim 2 wherein $R_2$ is H or $CH_3$.

4. The compound according to claim 3 wherein X is $OR_8$ or $NR_6R_7$.

5. The compound according to claim 4 wherein Z is monocyclic.

6. The compound according to claim 5 wherein $R_1$ is selected from the group consisting of $CO_2H$, $C(O)NHOH$, $CO_2CH_3$, and $CO_2C_2H_5$.

7. The compound according to claim 6 wherein X is OH.

8. The compound according to claim 7 wherein n is 2 or 3 and Z is substituted phenyl or heteroaromatic ring.

9. The compound according to claim 8 wherein Z is substituted phenyl or substituted or unsubstituted thienyl.

10. The compound according to claim 9 wherein n is 2.

11. The compound according to claim 9 wherein Z is substituted with from 1 to about 4 substituents, said substituents being selected independently from the group consisting of halo, alkyl, haloalkyl, cyano, nitro, alkoxy, phenyl, and phenoxy.

12. The compound according to claim 1 wherein Z is substituted with from 1 to about 4 substituents, said substituents being selected independently from the group consisting of halo, alkyl, haloalkyl, cyano, nitro, alkoxy, phenyl, and phenoxy.

13. The compound according to claim 1 wherein said compound is selected from the group consisting of:

13,14-dihydro-17-(2,4-difluorophenyl)-17- trinor prostaglandin $F_{1\alpha}$ methyl ester;

13,14-dihydro-17-(2,4-difluorophenyl)-17-trinor prostaglandin $F_{1\alpha}$;

13,14-dihydro-17-(2-fluorophenyl)-17-trinor prostaglandin $F_{1\alpha}$ methyl ester;

13,14-dihydro-17-(2-fluorophenyl)-17-trinor prostaglandin $F_{1\alpha}$;

13,14-dihydro-17-(3-fluorophenyl)-17-trinor prostaglandin $F_{1\alpha}$ methyl ester;

13,14-dihydro-17-(3-fluorophenyl)-17-trinor prostaglandin $F_{1\alpha}$;

13,14-dihydro-17-(4-fluorophenyl)-17-trinor prostaglandin $F_{1\alpha}$ methyl ester;

13,14-dihydro-17-(4-fluorophenyl)-17-trinor prostaglandin $F_{1\alpha}$;

13,14-dihydro-17-(2-methoxyphenyl)-17-trinor prostaglandin $F_{1\alpha}$ methyl ester;

13,14-dihydro-17-(2-methoxyphenyl)-17-trinor prostaglandin $F_{1\alpha}$;

13,14-dihydro-17-(3-methoxyphenyl)-17-trinor prostaglandin $F_{1\alpha}$ methyl ester;

13,14-dihydro-17-(3-methoxyphenyl)-17-trinor prostaglandin $F_{1\alpha}$;

13,14-dihydro-17-(4-methoxyphenyl)-17-trinor prostaglandin $F_{1\alpha}$ methyl ester;

13,14-dihydro-17-(4-methoxyphenyl)-17-trinor prostaglandin $F_{1\alpha}$;

13,14-dihydro-17-(3,5-difluorophenyl)-17-trinor prostaglandin $F_{1\alpha}$.

14. The compound according to claim 1 wherein said compound is selected from the group consisting of:

13,14-dihydro-17-((2-trifluoromethyl)phenyl)-17-trinor prostaglandin $F_{1\alpha}$ methyl ester;

13,14-dihydro-17-((2-trifluoromethyl)phenyl)-17-trinor prostaglandin $F_{1\alpha}$;

13,14-dihydro-17-((3-trifluoromethyl)phenyl)-17-trinor prostaglandin $F_{1\alpha}$ methyl ester;

13,14-dihydro-17-((3-trifluoromethyl)phenyl)-17-trinor prostaglandin $F_{1\alpha}$;

13,14-dihydro-17-((4-trifluoromethyl)phenyl)-17-trinor prostaglandin $F_{1\alpha}$ methyl ester;

13,14-dihydro-17-((4-trifluoromethyl)phenyl)-17-trinor prostaglandin $F_{1\alpha}$.

15. The compound according to claim 1 wherein said compound is selected from the group consisting of:

13,14-dihydro-18-(2-thienyl)-18-dinor prostaglandin $F_{1\alpha}$, methyl ester;

13,14-dihydro-18-(2-thienyl)-18-dinor prostaglandin $F_{1\alpha}$.

16. A method of treating a human or other animal subject having a bone disorder, said method comprising administering to said subject a compound according to the structure:

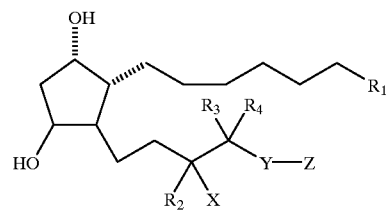

wherein (a) $R_1$ is $CO_2H$, $C(O)NHOH$, $CO_2R_5$, $CH_2OH$, $S(O)_2R_5$, $C(O)NHR_5$, $C(O)NHS(O)_2R_5$, or tetrazole; wherein $R_5$ is alkyl, heteroalkyl, carbocyclic aliphatic ring, heterocyclic aliphatic ring, aromatic ring, or heteroaromatic ring;

(b) $R_2$ is H or lower alkyl;

(c) X is $NR_6R_7$, $OR_8$, $SR_9$, $S(O)R_9$, $S(O)_2R_9$, or F; wherein $R_6$, $R_7$, and $R_8$ are independently selected from the group consisting of H, acyl, alkyl, heteroalkyl, carbocyclic aliphatic ring, heterocyclic aliphatic ring, aromatic ring, and heteroaromatic ring; and wherein $R_9$ is alkyl, heteroalkyl, carbocyclic aliphatic ring, heterocyclic aliphatic ring, aromatic ring, or heteroaromatic ring;

(d) $R_3$ and $R_4$ are independently H, $CH_3$, $C_2H_5$, $OR_{10}$, $SR_{10}$, or OH, except that both $R_3$ and $R_4$ are not OH; wherein $R_{10}$ is alkyl, heteroalkyl, carbocyclic aliphatic ring, heterocyclic aliphatic ring, aromatic ring, or heteroaromatic ring, $R_{10}$ having from 1 to about 8 member atoms;

(e) Y is $(CH_2)_n$; n being an integer from 0 to about 3;

(f) Z is carbocyclic aliphatic ring, heterocyclic aliphatic ring, aromatic ring, or heteroaromatic; and any optical isomer, diasteroemer, enantiomer of the above structure, or a pharmaceutically-acceptable salt, or biohydrolyzable amide, ester, or imide thereof.

17. The method of claim 16 wherein said bone disorder is osteoporosis.

18. The method of claim 17 wherein said bone disorder is post-menopausal.

19. The method of claim 17 wherein said bone disorder is cortico-steroid induced.

20. The method of claim 16 wherein said bone disorder is osteopenia.

21. The method of claim 16 wherein said bone disorder is a bone fracture.

22. The method of claim 16 wherein said compound is administered orally.

23. The method of claim 16 wherein said compound is administered transdermally.

24. The method of claim 16 wherein said compound is administered intranasally.

25. A method of treating glaucoma, said method comprising administering to a human or other animal a safe and effective amount of a compound according to the structure:

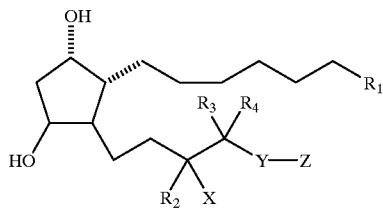

wherein (a) $R_1$ is $CO_2H$, $C(O)NHOH$, $CO_2R_5$, $CH_2OH$, $S(O)_2R_5$, $C(O)NHR_5$, $C(O)NHS(O)_2R_5$, or tetrazole; wherein $R_5$ is alkyl, heteroalkyl, carbocyclic aliphatic ring, heterocyclic aliphatic ring, aromatic ring, or heteroaromatic ring;

(b) $R_2$ is H or lower alkyl;

(c) X is $NR_6R_7$, $OR_8$, $SR_9$, $S(O)R_9$, $S(O)_2R_9$, or F; wherein $R_6$, $R_7$, and $R_8$ are independently selected from the group consisting of H, acyl, alkyl, heteroalkyl, carbocyclic aliphatic ring, heterocyclic aliphatic ring, aromatic ring, and heteroaromatic ring; and wherein $R_9$ is alkyl, heteroalkyl, carbocyclic aliphatic ring, heterocyclic aliphatic ring, aromatic ring, or heteroaromatic ring;

(d) $R_3$ and $R_4$ are independently H, $CH_3$, $C_2H_5$, $OR_{10}$, $SR_{10}$, or OH, except that both $R_3$ and $R_4$ are not OH; wherein $R_{10}$ is alkyl, heteroalkyl, carbocyclic aliphatic ring, heterocyclic aliphatic ring, aromatic ring, or heteroaromatic ring, $R_{10}$ having from 1 to about 8 member atoms;

(e) Y is $(CH_2)_n$; n being an integer from 0 to about 3;

(f) Z is carbocyclic aliphatic ring, heterocyclic aliphatic ring, heteroaromatic ring, substituted phenyl, or substituted or unsubstituted napthyl when n is 0, 2, or 3; and Z is carbocyclic aliphatic ring, heterocyclic aliphatic ring, substituted phenyl, or substituted or unsubstituted napthyl when n is 1; and any optical isomer, diasteroemer, enantiomer of the above structure, or a pharmaceutically-acceptable salt, or biohydrolyzable amide, ester, or imide thereof.

26. The method of claim 25 wherein said compound is administered topically.

* * * * *

UNITED STATES PATENT AND TRADEMARK OFFICE
CERTIFICATE OF CORRECTION

PATENT NO.    : 6,107,338
DATED         : August 22, 2000
INVENTOR(S)   : John August Wos et al.

It is certified that error appears in the above-identified patent and that said Letters Patent is hereby corrected as shown below:

Column 8,
Scheme I, bottom row, second group from left, of the issued patent, delete "$R_5$" and insert -- $R_6$ --.

Column 11,
Line 7, delete "15" and insert -- 18 --.

Column 24,
Line 28, Example 21, insert -- - -- after the number "17" and before the word "trinor".

Column 41,
Line 57, delete "1" and insert -- 11 --.

Signed and Sealed this

Twenty-third Day of September, 2003

JAMES E. ROGAN
*Director of the United States Patent and Trademark Office*